(12) United States Patent (10) Patent No.: US 8,932,243 B2
Calabrese (45) Date of Patent: Jan. 13, 2015

(54) CERVICAL COLLAR WITH INDEPENDENT HEIGHT AND CIRCUMFERENCE ADJUSTABILITY

(76) Inventor: Salvatore Calabrese, Aldan, PA (US)

( * ) Notice: Subject to any disclaimer, the term of this patent is extended or adjusted under 35 U.S.C. 154(b) by 195 days.

(21) Appl. No.: 13/331,968

(22) Filed: Dec. 20, 2011

(65) Prior Publication Data

US 2012/0165712 A1 Jun. 28, 2012

Related U.S. Application Data

(60) Provisional application No. 61/425,108, filed on Dec. 20, 2010.

(51) Int. Cl.
*A61F 5/00* (2006.01)
*A61F 5/055* (2006.01)
(52) U.S. Cl.
CPC ...................................... *A61F 5/055* (2013.01)
USPC ............................................................ 602/18
(58) Field of Classification Search
USPC ........... 602/5, 17, 18, 19; 128/DIG. 23; 2/468
See application file for complete search history.

(56) References Cited

U.S. PATENT DOCUMENTS

| | | | |
|---|---|---|---|
| 2,735,424 A | 2/1956 | Benjamin |
| 2,801,630 A | 8/1957 | Moore |
| 2,806,471 A | 9/1957 | Breese |
| 2,911,970 A | 11/1959 | Bartels |
| D188,302 S | 6/1960 | Monfardini |
| 3,024,784 A | 3/1962 | Monfardini |
| 3,027,894 A | 4/1962 | Moore |
| 3,042,027 A | 7/1962 | Monfardini |
| 3,050,052 A | 8/1962 | Grassl et al. |
| 3,060,930 A | 10/1962 | Grassl |
| 3,075,521 A | 1/1963 | Grassl |
| 3,135,256 A | 6/1964 | Gruber |
| D203,018 S | 11/1965 | Helferich |
| 3,285,244 A | 11/1966 | Cottrell |
| 3,306,284 A | 2/1967 | McKinley |
| 3,313,297 A | 4/1967 | Applegate et al. |
| 3,512,523 A | 5/1970 | Barnett |
| 3,756,226 A | 9/1973 | Calabrese et al. |
| 3,916,884 A | 11/1975 | Attenburrow |

(Continued)

OTHER PUBLICATIONS

PCT International Search Report, PCT/US2011/066220, Apr. 12, 2012, 4 pp., International Searching Authority.

*Primary Examiner* — Patricia Bianco
*Assistant Examiner* — Raymond E Harris
(74) *Attorney, Agent, or Firm* — Blank Rome LLP

(57) ABSTRACT

An adjustable cervical collar designed to accommodate a broad range of prospective wearers with unique physical attributes, and to restrict the movements of the wearer's cervical spine, including rotation, flexion, extension, and lateral bending. The cervical collar includes a front portion and back portion, which may be adjusted in relation to one other to vary the circumference of the cervical collar. The front portion includes upper and lower plastic portions which may be adjusted to vary the height of the cervical collar, and a front thoracic extender which may be adjusted to achieve a desired restrictiveness of flexion movement. The back portion includes occipital and back thoracic extenders which may be adjusted to achieve a desired restrictiveness of extension movement. The adjustable features may be operated independently of one another. The adjustable features include locking means to ensure that the cervical collar is securely applied to the wearer.

22 Claims, 18 Drawing Sheets

(56) References Cited

U.S. PATENT DOCUMENTS

| | | | | |
|---|---|---|---|---|
| 3,916,885 | A | 11/1975 | Gaylord, Jr. | |
| 4,099,523 | A | 7/1978 | Lowrey | |
| 4,383,523 | A * | 5/1983 | Schurman | 602/36 |
| 4,520,801 | A | 6/1985 | Lerman | |
| 4,538,597 | A | 9/1985 | Lerman | |
| 4,582,051 | A | 4/1986 | Greene et al. | |
| 4,955,368 | A | 9/1990 | Heimann | |
| 5,005,563 | A | 4/1991 | Veale | |
| 5,201,702 | A * | 4/1993 | Mars | 602/17 |
| 5,230,698 | A | 7/1993 | Garth | |
| 5,433,696 | A | 7/1995 | Osti | |
| 5,520,619 | A | 5/1996 | Martin | |
| 5,593,382 | A | 1/1997 | Rudy, Jr. et al. | |
| 5,688,229 | A | 11/1997 | Bauer | |
| 5,728,054 | A | 3/1998 | Martin | |
| D393,718 | S | 4/1998 | Traut et al. | |
| 5,785,670 | A | 7/1998 | Hiebert | |
| 5,788,658 | A | 8/1998 | Islava | |
| 5,795,315 | A | 8/1998 | Traut et al. | |
| 5,865,773 | A * | 2/1999 | Koledin | 602/18 |
| 5,964,722 | A | 10/1999 | Goralnik et al. | |
| 5,993,403 | A | 11/1999 | Martin | |
| 6,036,664 | A | 3/2000 | Martin, Sr. et al. | |
| RE36,745 | E | 6/2000 | Rudy | |
| 6,090,058 | A | 7/2000 | Traut et al. | |
| 6,245,033 | B1 | 6/2001 | Martin | |
| 6,254,560 | B1 | 7/2001 | Tweardy et al. | |
| 6,315,746 | B1 * | 11/2001 | Garth et al. | 602/18 |
| 6,423,020 | B1 | 7/2002 | Koledin | |
| 6,663,581 | B1 | 12/2003 | Calabrese | |
| 6,726,643 | B1 | 4/2004 | Martin | |
| 6,770,046 | B2 | 8/2004 | Hansen | |
| 6,921,376 | B2 * | 7/2005 | Tweardy et al. | 602/18 |
| 7,041,073 | B1 | 5/2006 | Patron | |
| 7,399,288 | B2 | 7/2008 | Chao | |
| 7,442,176 | B2 | 10/2008 | Cojbasic | |
| 7,674,234 | B2 | 3/2010 | Calco et al. | |
| 7,878,995 | B2 | 2/2011 | Harty | |
| 7,981,068 | B2 | 7/2011 | Thorgilsdottir et al. | |
| 8,038,635 | B2 | 10/2011 | Dellanno | |
| 8,038,636 | B2 | 10/2011 | Thorgilsdottir et al. | |
| 2010/0137768 | A1 * | 6/2010 | Thorgilsdottir et al. | 602/18 |

* cited by examiner

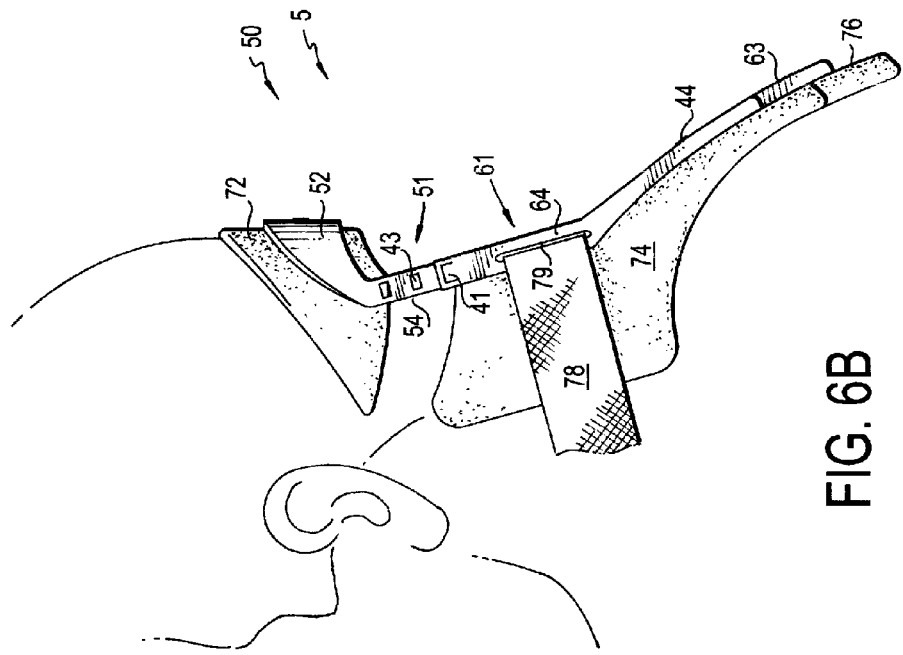
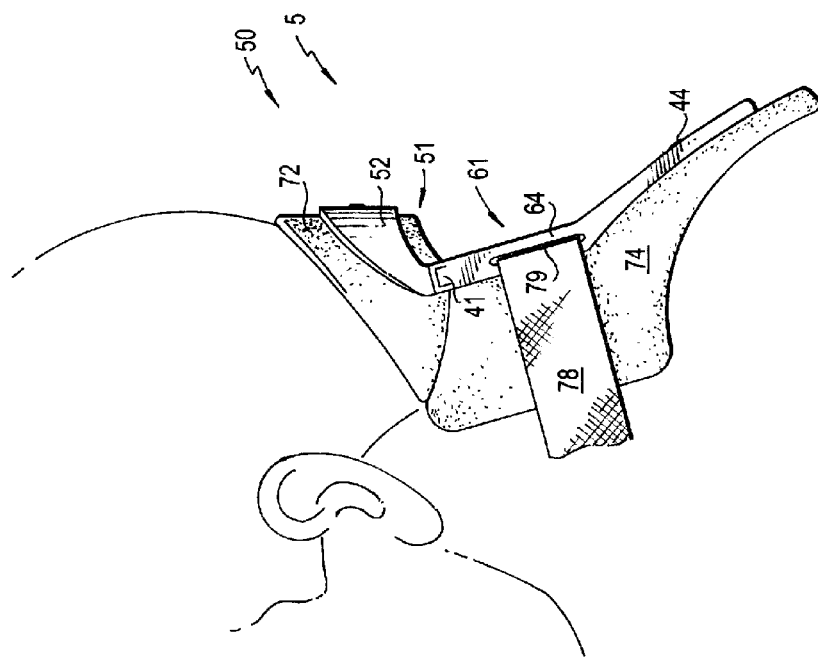

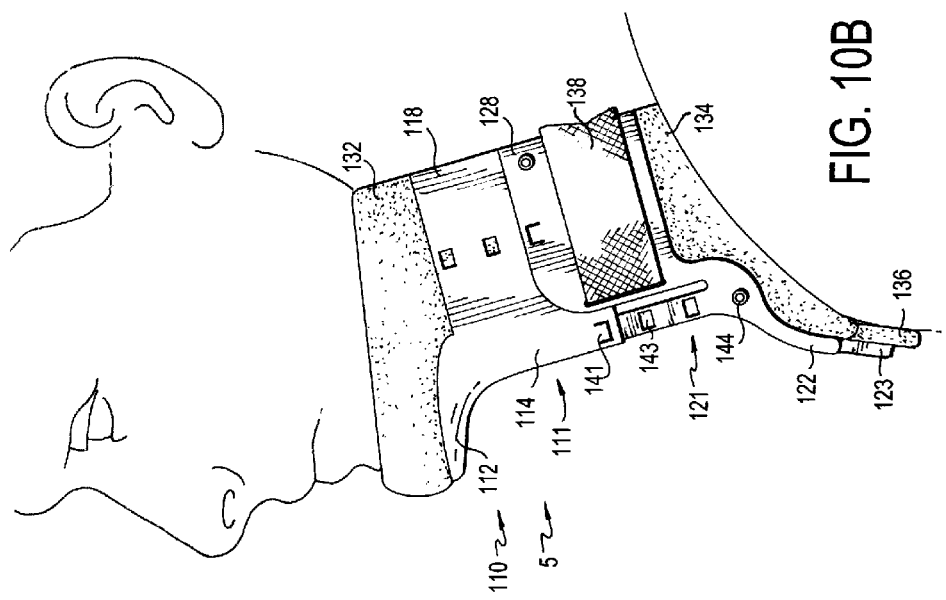
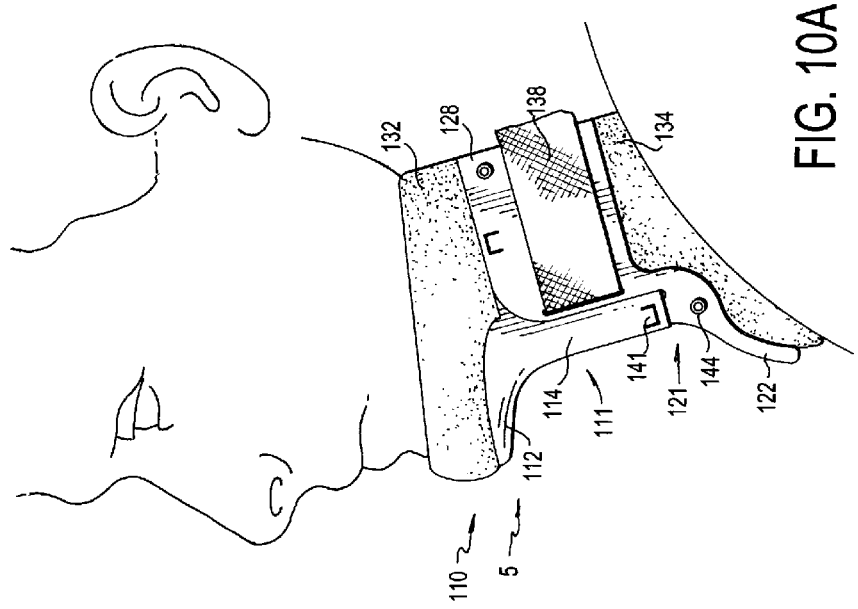

CERVICAL COLLAR WITH INDEPENDENT HEIGHT AND CIRCUMFERENCE ADJUSTABILITY

CROSS REFERENCE TO RELATED APPLICATION

This patent application claims the benefit of U.S. Provisional Patent Application No. 61/425,108 filed Dec. 20, 2010, the entirety of which is incorporated herein by reference.

BACKGROUND OF THE INVENTION

1. Field of the Invention

The present invention relates generally to cervical collars. In particular, the present invention relates to cervical collars that are capable of being independently adjusted in height and circumference, as well as independently adjustable with thoracic and occipital extensions, to accommodate unique physical attributes of the heads and necks of various individual wearers.

2. Description of the Related Art

Cervical collars have been developed to limit the range of motion of the cervical spine of an individual who has sustained trauma to the head and/or neck as a result of an accident, illness or injury. Movement of the cervical spine is designated into four specific categories: flexion (chin downward motion); extension (chin upward motion); rotation (chin left-to-right/right-to-left motion); lateral bending (ear to shoulder motion); and any combinations thereof. The primary roles of a cervical collar are to support its wearer's head in a neutral or specifically designated position relative to the wearer's neck and torso, and to restrict the wearer's movement therein. These roles are accomplished by selecting and applying a cervical collar that is appropriately measured and sized, commensurate with the unique physical attributes of the head and neck of the wearer. To ensure the cervical collar is properly sized, two physical measurements of the wearer must be considered: the height from the bottom of the chin to the top of the sternum; and the circumference of the neck at its midline. These measurements correspond to a specifically sized cervical collar. An improperly sized cervical collar may not properly support the head of its wearer, thereby allowing unwanted head movement and causing further injury.

Many cervical collars, such as those shown in U.S. Pat. Nos. 3,756,226, 5,230,698 and 6,254,560, are manufactured and commercially offered in a range of individual sizes, which combine various heights and circumferences to accommodate the unique physical attributes of a broad range of prospective wearers. Those products are typically designated as "sized" cervical collars. For example, when a healthcare provider is selecting an appropriately sized cervical collar for an adult patient, he will have to choose from amongst up to about twenty variously sized cervical collars described in U.S. Pat. No. 3,756,226, fifteen variously sized cervical collars described in U.S. Pat. No. 5,230,698, or seven variously sized cervical collars described in U.S. Pat. No. 6,254,560. Thus, to establish, maintain, and replenish a complete inventory of any of those adult cervical collars (not to mention their infant and pediatric sizes) is extremely costly. Furthermore, an excessive amount of space is necessary to store the material. In emergency transport vehicles such as ambulances, there is a minimal space allocation, and it is difficult to store all the various sizes of "sized" cervical collars. When a properly sized cervical collar is unavailable, a healthcare provider may apply an improperly sized cervical collar to a patient, thereby increasing the risk of injury. Even when a sufficient inventory of cervical collars is available, an inexperienced healthcare provider may inadvertently select the wrong size cervical collar, which also increases the patient's risk of injury.

In an attempt to overcome the above shortcomings associated with "sized" cervical collars, other manufacturers have developed cervical collars, such as those shown in U.S. Pat. Nos. 5,433,696, 7,674,234 and 7,981,068, having means for adjusting the height and circumference of the cervical collars, thereby reducing the amount of unique cervical collars required for the manufacturers' specific product lines. Those products are typically designated as "universal" cervical collars. However, in their attempt to serve as one-size-fits-all products, those cervical collars exhibit other design shortcomings which can cause a wearer injury.

For example, some universal cervical collars include components that may become lost or separated from the cervical collar, thereby rendering the cervical collar useless. U.S. Pat. No. 5,433,696, for example, describes a universal cervical collar in which the height adjustment mechanism, including a separate spacer is secured by separate tightening screws used to lock various elements to one another. Accordingly, that cervical collar requires a separate tool, such as a screwdriver, to properly lock the cervical collar into position. As a practical matter, and given the often urgent circumstances under which cervical collars must be applied, a healthcare provider will often be allowed insufficient time to assemble that cervical collar without the risk of potential failure, and future injury to the wearer.

In another example, a healthcare provider may select a cervical collar as described in U.S. Pat. No. 7,674,234. Unfortunately, as a result of its geared height adjustment mechanism, that cervical collar does not provide adequate support of the mandible throughout the height adjustment range, and thereby permits excessive lateral bending and rotational movement. Another serious consequence of that cervical collar's height adjustment mechanism is that, as height increases, the mechanism distorts the relative neutral position and places the wearer in hyper-extension, thus causing the wearer injury.

In yet another example, a healthcare provider may select a cervical collar as described in U.S. Pat. No. 7,981,068, which includes a removable height support mechanism. That mechanism is intentionally separate from the main cervical collar and requires a separate locking button to connect the mechanism to the main cervical collar. As stated in U.S. Pat. No. 7,981,068, the adjustable height support mechanism is configured to be removable from the cervical collar to allow for maintenance, or cleaning around the area. However, as with the cervical collar of U.S. Pat. No. 5,433,696, components that can be separated from the cervical collar are easily misplaced, mishandled, and often lost, rendering the cervical collar useless. When a cervical collar, such as the one described in U.S. Pat. No. 7,981,068 is applied to a patient, and a component of the cervical collar is unable to be reattached, the patient may be put at risk of serious and potentially life threatening injury. Furthermore, as with most collars the cervical collar of U.S. Pat. No. 7,981,068 relies on the wearer's shoulders for support of the cervical collar to restrict lateral movement. When the height support of that cervical collar is adjusted (i.e., the height of the cervical collar is increased), the cervical collar is caused to lift off of the shoulders of the wearer, thereby interfering with the overall support of the cervical collar and consequently resulting in unnecessary lateral movement possibly causing injury to the wearer.

The examples above indicate a need for a cervical collar that, in addition to offering multiple sizes in a single cervical collar, must be easy to use and apply to a wearer, must sufficiently maintain neutral alignment and limit the range of motion of the cervical spine, and must not require separate individual components which may become lost, thereby rendering the cervical collar useless. Furthermore, the individual height adjustment and circumference adjustment must function independently of one another to accommodate the unique physical attributes of each prospective wearer.

Another requirement of a cervical collar is that the cervical collar should not be lacking in any qualities associated with cervical spine stabilization, specifically those related to flexion and extension. Rather, the cervical collar should include features that serve to enhance the limitation of the wearer's motion.

Furthermore, due to the ever-present goal of the healthcare industry to produce low cost, high quality products, additional consideration must be given to the cost, and the difficulty, associated with manufacturing the cervical collar. Due to the complexity of their height adjustment mechanisms, many commercially offered cervical collars require numerous parts. For example, the aforementioned cervical collar described in U.S. Pat. No. 7,674,234, utilizes a variety of separately manufactured components such as pawls, rows of ratchet teeth, and a locking button sub-assembly mechanism, which substantially increases the manufacturing cost of the cervical collar. That example is indicative of the need for a single cervical collar that can accommodate a wide range of various sizes and is cost effective.

Finally, the efficacy of a cervical collar is largely attributable to wearer compliance, which requires the cervical collar to be anatomically shaped, contoured, and properly ventilated, while providing sufficient support and comfort to allow the cervical collar to maintain the wearer's head in a neutral position relative to the neck and torso, and restrict the wearer's movement.

Therefore, there is a need for a cervical collar that is capable of being independently adjusted in height and circumference to accommodate the unique physical attributes of a broad range of prospective wearers, and that includes additional features that serve to enhance the limitation of the wearers' motion. In particular, there is a need for a cervical collar that includes a frontal thoracic extender that significantly reduces flexion, and occipital and rear thoracic extenders that significantly reduce extension. These additional components should be non-removable, retractable, and independently adjustable so that the features provide the precise degree of restriction of movement deemed necessary by a healthcare provider.

SUMMARY OF THE INVENTION

Accordingly, it is an object of the present invention to provide a cervical collar that limits the range of motion of a wearer's cervical spine in flexion, extension, rotation, lateral bending, and any combinations thereof.

It is another object of the present invention to provide a cervical collar that provides support to the wearer's cervical spine.

It is yet another object of the present invention to provide a cervical collar that can be adjusted to accommodate the various individual and unique physical attributes of the head and neck of the wearer.

It is yet another object of the present invention to provide a cervical collar that includes a mechanism for adjusting the height of the front portion of the cervical collar in an essentially vertical manner, independent of other cervical collar components.

It is yet another object of the present invention to provide a cervical collar that includes a mechanism to adjust the height of the back portion of the cervical collar in an essentially vertical manner, independent of other cervical collar components.

It is yet another object of the present invention to provide a cervical collar that includes a mechanism to adjust a thoracic extender of the front portion of the cervical collar in an essentially vertical manner, independent of other cervical collar components.

It is yet another object of the present invention to provide a cervical collar that includes a mechanism to adjust a thoracic extender of the back portion of the cervical collar in an essentially vertical manner, independent of other cervical collar components.

It is still a further object of the present invention to provide a cervical collar that allows sufficient access to the neck of the wearer.

It is yet another object of the present invention to provide a cervical collar that includes a mechanism that allows its circumference to be adjusted by adjusting the front and back portions, or both, of the cervical collar in an essentially horizontal manner independent of other cervical collar components.

Those and other objects may be achieved by a cervical collar comprising: a first upper plastic portion; a first lower plastic portion; a first thoracic extender; a sliding connection between the upper plastic portion and the lower plastic portion that allows the first upper plastic portion to be adjusted and secured with respect to the first lower plastic portion; and a sliding connection between the first thoracic extender and the first lower plastic portion that allows the first thoracic extender to be adjusted and secured with respect to the first lower plastic portion. The cervical collar may further include a front portion comprising the first upper plastic portion and the first lower plastic portion; a back portion; and a fastening device connecting the front portion to the back portion, wherein the fastening device allows the back portion to be adjusted and secured with respect to the front portion.

The back portion may further comprise: a second upper plastic portion; a second lower plastic portion; and a sliding connection between the second upper plastic portion and the second lower plastic portion that allows the second upper plastic portion to be adjusted and secured with respect to the second lower plastic portion. The back portion may further comprise: a second thoracic extender; and a sliding connection between the second thoracic extender and the second lower plastic portion that allows the second thoracic extender to be adjusted and secured with respect to the second lower plastic portion. Both the front and back portions may include separate padding, wherein the padding is formed of a different material than the first and second upper plastic portions, and the first and second lower plastic portions.

BRIEF DESCRIPTION OF THE DRAWINGS

Many aspects of the present invention can be better understood with reference to the accompanying drawings, which are part of the specification and represent exemplary embodiments of the present invention. The components in the drawings are not necessarily to scale, emphasis instead being placed upon illustrating the principles of the present invention.

FIGS. 6A and 6B are side elevation views of the back portion of a cervical collar in accordance with an exemplary embodiment of the present invention.

FIGS. 10A and 10B are side elevation views of the front portion of a cervical collar in accordance with an exemplary embodiment of the present invention.

DETAILED DESCRIPTION OF THE PREFERRED EMBODIMENTS

Figure 1A:
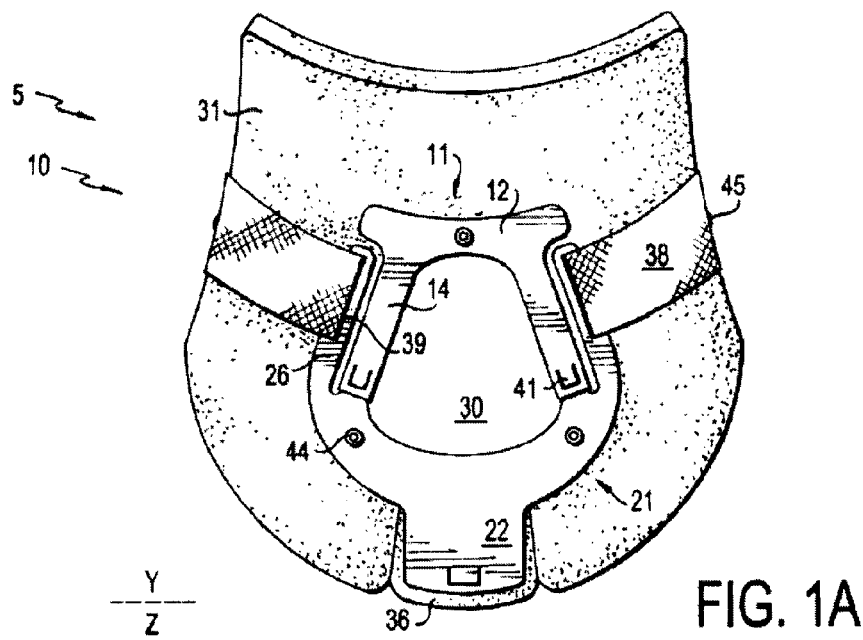
FIGS. 1A and 1B are front elevation views of the front portion of a cervical collar in accordance with an exemplary embodiment of the present invention.

In describing the preferred embodiments of the present invention illustrated in the drawings, specific terminology will be resorted to for the sake of clarity. However, the present invention is not intended to be limited to the specific terms so selected, and it is to be understood that each specific term includes all technical equivalents that operate in a similar manner to accomplish a similar purpose.

Referring to FIGS. 1A, 1B, 5A, and 5B, the cervical collar 5 of the present invention includes a front portion 10 and a separate and distinct back portion 50 that, when used together, secure a wearer's head and neck to limit the wearer's flexion, extension, rotation, and lateral movement. Preferably, the front portion 10 and the back portion 50 each include injection molded, substantially incompressible, plastic material components such as polyethylene or nylon to increase the restrictive properties of the cervical collar 5. Preferably, the front portion 10 and the back portion 50 each also include semi-rigid foam material components, such as polyethylene or polyester, to add structure to the cervical collar 5 and to provide comfort to the wearer. In normal use, the rigid plastic material components are intended not to deform or distort when a force is applied to the material, and the semi-rigid foam material components are intended to maintain an initial general shape after an applied force has deformed or distorted to the material. Varying the thickness of the plastic material may alter its functionality. For example, an increase in thickness will make the plastic material more rigid and stiff, while a decrease in thickness will make the plastic material more flexible and pliable. Increased rigidity may also be accomplished by incorporating perpendicular ribs onto the plastic material. Conversely, increased flexibility may be accomplished by incorporating openings, holes, or slots into the plastic material. Portions of the plastic material can also be adjusted independently to increase rigidity and/or flexibility as desired.

In a preferred embodiment, the front portion 10 and the back portion 50 are independently adjustable with respect to each other to accommodate the unique neck height and neck circumference of an individual wearer, and to allow for independent modification of the wearer's range of motion. Accordingly, the front portion 10 and the back portion 50 are preferably connected to each other at their respective distal ends by adjustable mechanical fasteners that form an encircling band around the wearer's neck. Both the front portion 10 and back portion 50 are each horizontally symmetrical along their vertical axes, such that each right and left opposing feature is essentially identical.

Figure 1B:
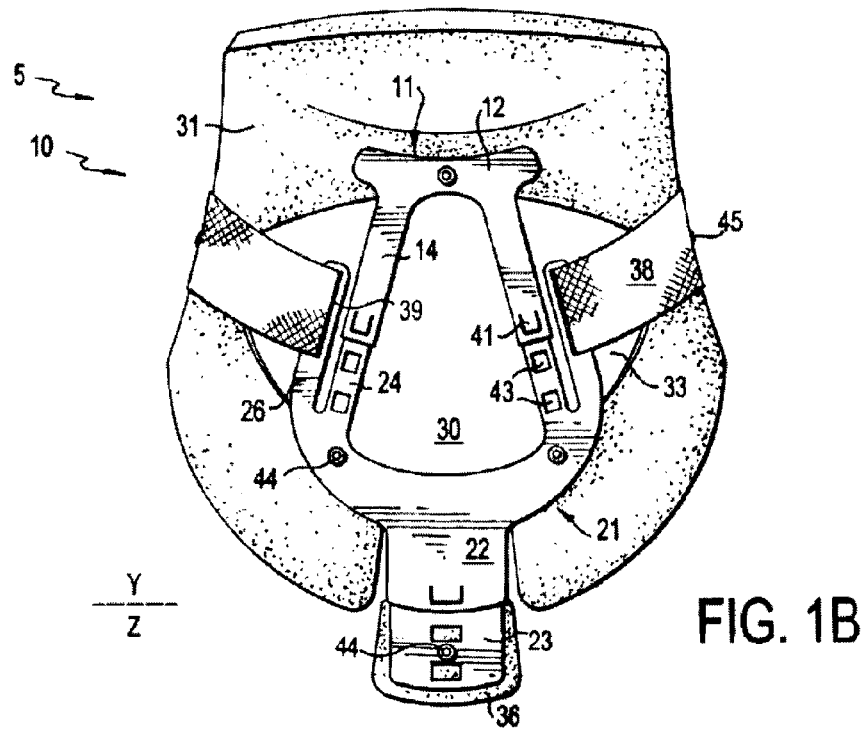

With continued reference to the exemplary embodiment of the front portion 10 of the cervical collar 5 illustrated in FIGS. 1A and 1B, the front portion 10 includes a front upper plastic portion 11 and a front lower plastic portion 21. Preferably, the front upper plastic portion 11 and the front lower plastic portion 21 are fabricated from substantially incompressible plastic resin, and injection molded in their final configurations as three dimensional components. The materials selected for the front upper plastic portion 11 and a front lower plastic portion 21 may be the same, or may be different.

The front upper plastic portion 11 includes an upper central chin support 12. Preferably, the chin support 12 is curved to conform generally to the shape of the wearer's chin. The chin support 12 includes a generally horizontal, concave surface to accept and support a wearer's chin, and serves to limit rotational movement. The chin support 12 accommodates a securely affixed front foam insert 31, which is configured to be positioned between the chin support 12 and the wearer's chin. The front foam insert 31 may be fabricated into a three dimensional shape by a separate manufacturing process, such as heated vacuum forming or a matched press. Fastening means 44, such as rivet bosses with cooperative rivets, may securely affix the front foam insert 31 to the front upper plastic portion 11. The chin support 12 may also include a lower perpendicular member (not shown) to increase rigidity. The distal ends (though not necessarily the extreme distal ends) of the lower edge of the chin support 12 are integrally connected to opposing right and left lateral elongated vertical upper height adjustment supports 14. Preferably, the upper height adjustment supports 14 are injection molded, and extend downwardly, substantially orthogonally, from the chin support 12. Accordingly, the front upper plastic portion 11 is preferably formed from a single unitary piece of plastic.

Figure 4A:
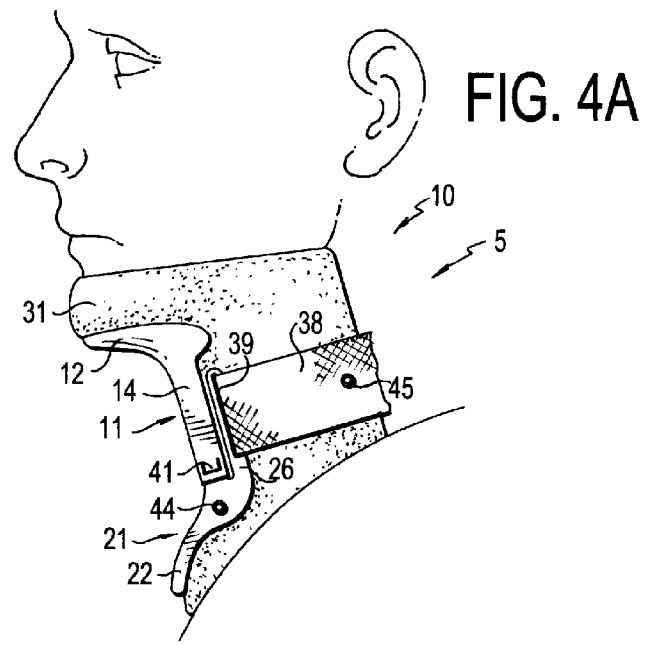
FIGS. 4A, 4B, and 4C are side elevation views of the front portion of a cervical collar in accordance with an exemplary embodiment of the present invention.
Figure 4B:
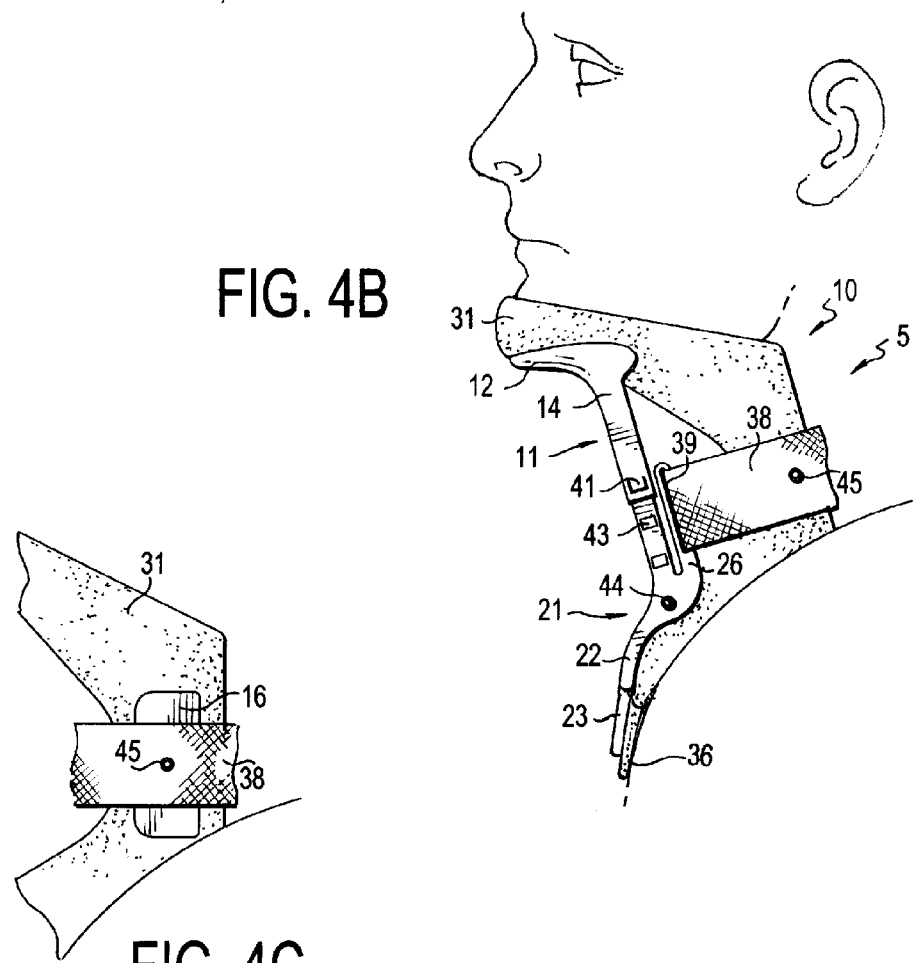

The front lower plastic portion 21 includes a sternum support 22. The sternum support 22 is an essentially vertical surface that rests at the top of the wearer's sternum. In FIGS. 1A and 1B, the cervical spine region is designated as region Y, and the thoracic spine region is designated as region Z. Generally, the top of the sternum is located below the wearer's cervical region, at a height corresponding to that of the first thoracic vertebra. The sternum support 22 assists in the restriction of flexion movement and accommodates a securely affixed foam insert 31. The foam insert 31 may be securely affixed to the sternum support by a fastening means 44 such as a rivet boss with a cooperative rivet. The sternum support 22 may be curved to conform generally to the shape of the wearer's anatomy. For example, as shown in FIGS. 4A and 4B, the lower portion of the sternum support 22 may curve outwardly to conform to the wearer's upper chest. The upper portion of the sternum support 22 may be curved to conform to the generally cylindrical shape of the wearer's neck. The upper portion of the sternum support 22 may have a width that is greater than the width of the lower portion of the sternum support 22. Opposing right and left lateral elongated vertical lower height adjustment supports 24 extend outwardly and upwardly from the distal ends (though not necessarily the extreme distal ends) of the upper edge of the sternum support 22. The lower height adjustment supports 24 are integrally connected to the sternum support 22. Preferably, the lower height adjustment supports 24 are injection molded, and extend upwardly from the sternum support 22. Accordingly, the front lower plastic portion 21 is preferably formed from a single unitary piece of plastic.

Figures 2A, 2B:
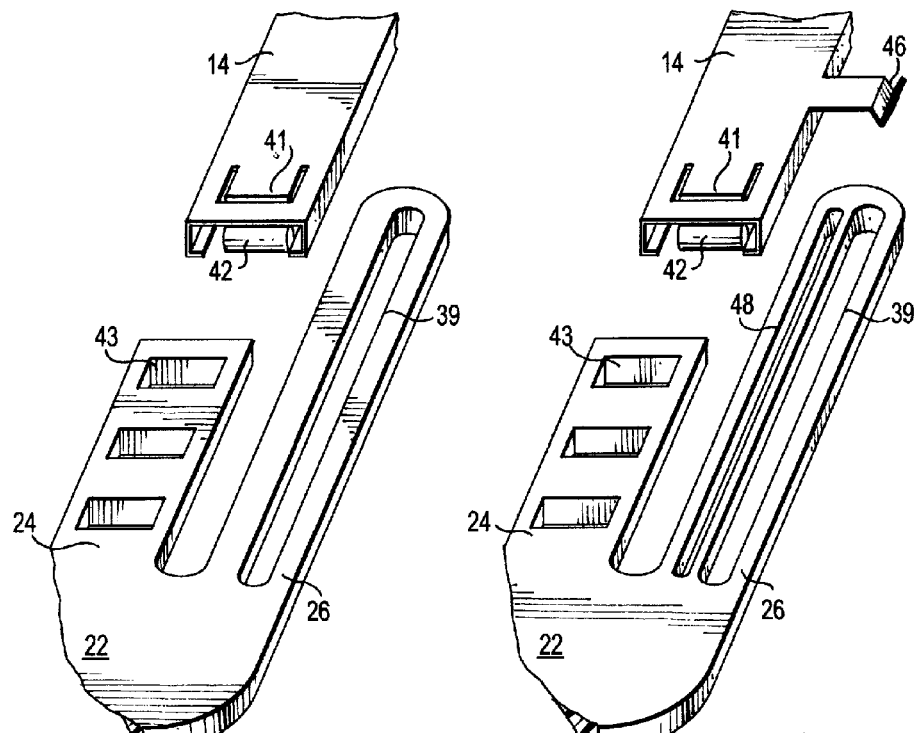
FIG. 2A is an exploded view of upper and lower height adjustment supports in accordance with an exemplary embodiment of the present invention.
FIG. 2B is an exploded view of upper and lower height adjustment supports in accordance with an exemplary embodiment of the present invention.

As illustrated in FIG. 2A, the terminal ends of the upper height adjustment supports 14 each include an outer surface, an inner surface, and opposing side surfaces with tabs extending inwardly toward each other, thereby forming a partially enclosed channel capable of slidably accepting the lower height adjustment support 24. The terminal end of each lower height adjustment support 24 is dimensionally similar to the inside dimension of the corresponding upper height adjustment support 14 to provide for a form-fitted, slidable connection between the lower height adjustment support 24 and the upper height adjustment support 14. Alternatively, the lower height adjustment supports 24 may be configured to slidably receive the upper height adjustment supports 14. The upper height adjustment supports 14 and lower height adjustment supports 24 collectively include a means for securely locking the upper height adjustment supports 14 with respect to the lower height adjustment supports 24. For example, each upper height adjustment support 14 may include an integrally connected, pivotably moveable lock tab 41 having a lock boss 42. The lock tab 41 and the lock boss 42 may be integrally formed, or may be securely affixed separate components. Each lower height adjustment support 24 may include a series of lock openings 43 to accept the cooperative upper height adjustment support lock boss 42, and lock the front upper plastic portion 11 at a desired height with respect to the front lower plastic portion 21.

As shown in FIG. 2B, the lower height adjustment support 24 may include a groove 48 that is configured to slidably receive a guide tongue 46 disposed on the upper height adjustment support 14. The slidable tongue-in-groove configuration provides structural support and stability to the front portion 10, and keeps the upper front plastic portion 11 and the front lower plastic portion 21 properly aligned as the height of the cervical collar 5 is adjusted.

Figure 3:
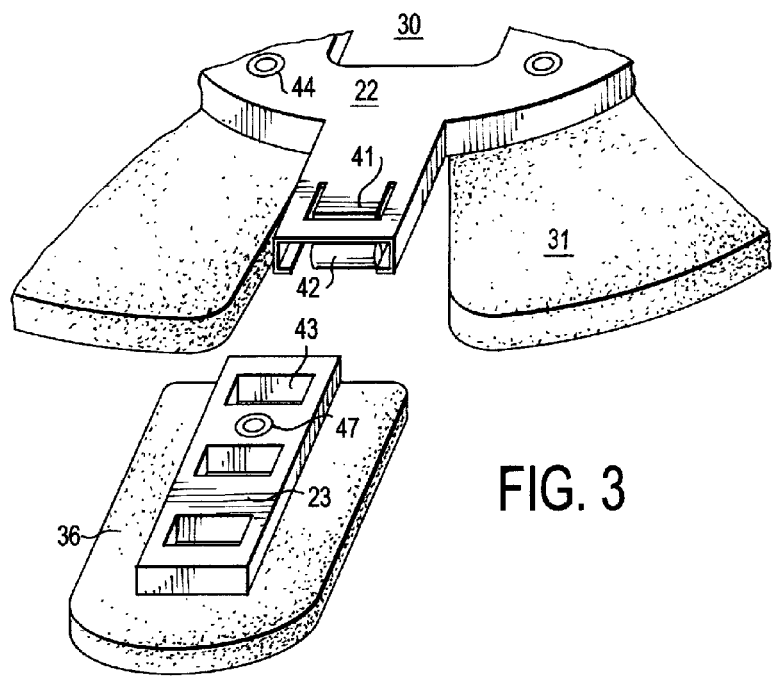
FIG. 3 is an exploded view of a front thoracic extender in accordance with an exemplary embodiment of the present invention.

Returning to FIGS. 1A and 1B, the sternum support 22 also includes a slidably connected front thoracic extender 23. As illustrated in FIG. 3, the terminal end of the sternum support 22 includes an outer surface, an inner surface, and opposing side surfaces with tabs extending inwardly toward each other, thereby forming a partially enclosed channel capable of accepting the front thoracic extender 23. The front thoracic extender 23 is a separate component, dimensionally similar to the inside dimension of the terminal end of the sternum support 22 to provide for a form-fitted, slidable connection between the front thoracic extender 23 and the sternum support 22. The front thoracic extender 23 includes a securely affixed front thoracic foam insert 36 to provide comfort to the wearer. The sternum support 22 and the front thoracic extender 23 collectively include a means for securely locking the front thoracic extender 23 with respect to the sternum support 22. For example, the sternum support 22 may include an integrally connected, pivotably moveable lock tab 41 having a lock boss 42. The lock tab 41 and the lock boss 42 may be integrally formed, or may be securely affixed separate components. The front thoracic extender 23 may include a series of lock openings 43 to accept the cooperative sternum support lock boss 42, and lock the front thoracic extender 23 at a desired height with respect to the sternum support 22.

The front lower plastic portion 21 further includes two opposing lateral fastener material supports 26 connected at the extreme distal ends of upper edge of the sternum support 22, although the fastener material supports 26 may be connected at any suitable location. As shown, for example, in FIGS. 1A, 1B, 4A, and 4B, the distal ends of upper edge of the sternum support 22 are integrally connected to opposing right and left lateral fastener material supports 26. Preferably, the fastener material supports 26 are injection molded and extend upwardly from the sternum support 22. Each fastener material support 26 is configured to securely affix a fastener material 38, such as hook-and-loop and the like, to the front lower plastic portion 21. The fastener material support 26 preferably includes a fastener material opening 39, as shown in FIG. 2A, to receive a free end of the fastener material 38 to be inserted, wrapped, and securely affixed to the fastener material support 26. The other end of the fastener material 38 is securely affixed to the front foam insert 31, such that the fastener material 38 maintains a substantially horizontal alignment relative to the front portion 10. Either end of the fastener material 38 may be securely affixed to the front portion 10 by a fastener, such as washer 45 with a cooperative rivet.

Figure 4C:
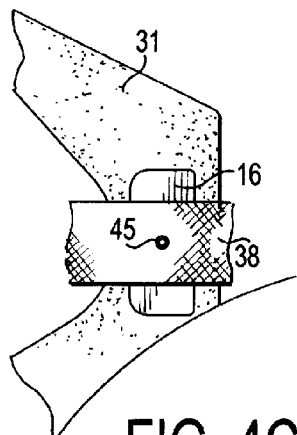

As illustrated in FIG. 4C, a lateral support 16 may be included at each distal end of the front portion 10 to further restrict the wearer's lateral movement. Preferably, the lateral supports 16 are fabricated from substantially incompressible plastic resin. The lateral supports 16 are substantially planar portions positioned along the right and left sides of the wearer's neck. However, the lateral supports 16 may be curved to conform to the generally cylindrical shape of the wearer's neck. The lateral supports 16, along with the fastener material 38 may be securely affixed to the front foam insert 31 by a fastener, such as washer 45 with a cooperative rivet. The lateral supports 16 may extend to and connect with the fastener material supports 26 to further restrict lateral movement.

When assembled, the front portion 10, as best shown in FIGS. 1A and 1B, includes a tracheal opening 30 which is defined by the lowermost edge of the chin support 12, the proximal edges of the upper height adjustment supports 14, the proximal edges of the lower height adjustment supports 24 and the uppermost edge of the sternum support 22. The area of the tracheal opening 30 incrementally increases as the height of the front portion 10 is adjusted from a first lowest position, as shown in FIG. 1A, to a final highest position, as shown in FIG. 1B. In some instances, the front foam insert 31 may partially extend into the tracheal opening 30 to provide additional comfort to the user.

Figure 5A:
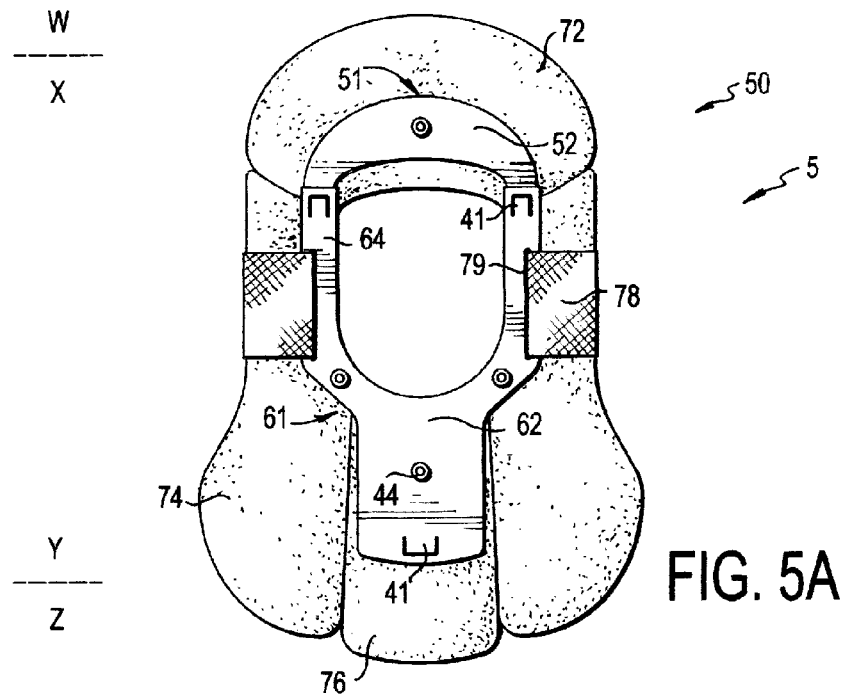
FIGS. 5A and 5B are rear elevation views of the back portion of a cervical collar in accordance with an exemplary embodiment of the present invention.
Figure 5B:
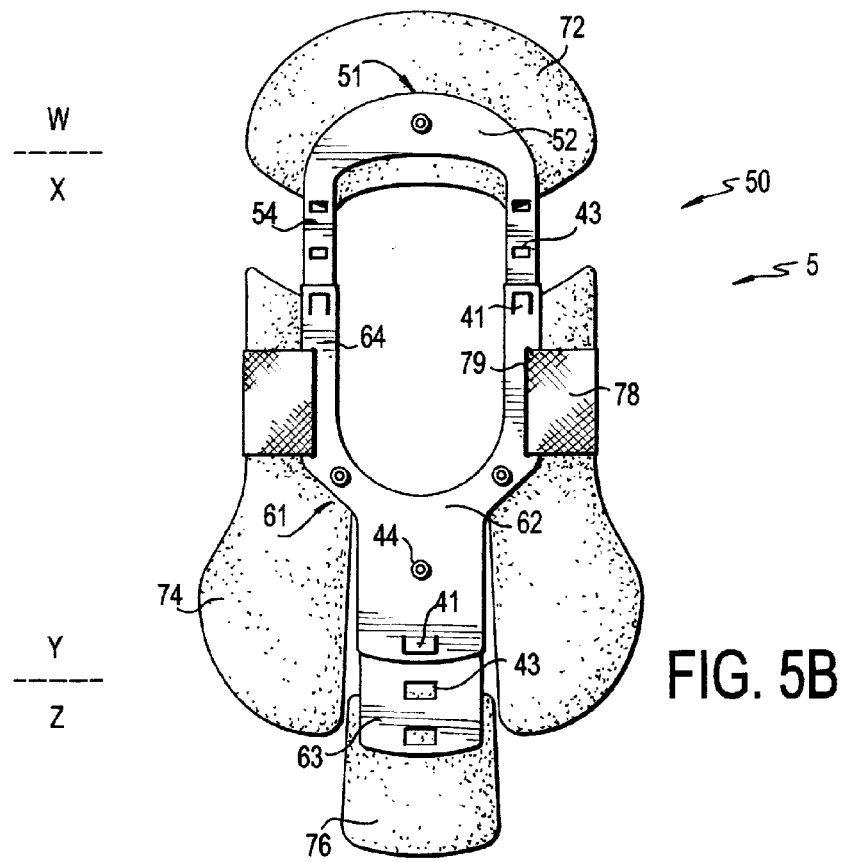

Turning to FIGS. 5A and 5B, shown therein is an exemplary embodiment of the back portion 50 of the cervical collar 5. The back portion 50 includes a back upper plastic portion 51 and a back lower plastic portion 61. Preferably, the back upper plastic portion 51 and the back lower plastic portion 61 are fabricated from substantially incompressible plastic resin and injection molded in their final configurations as three dimensional components. The materials selected for the back upper plastic portion 51 and a back lower plastic portion 61 may be the same, or may be different.

The back upper plastic portion 51 includes an upper central occipital support 52. Preferably, the occipital support 52 is curved to conform generally to the shape of the base of the wearer's head. The occipital support may curve outwardly from the back of the wearer's neck, as shown in FIGS. 6A and 6B, and extend substantially horizontally across the back of the wearer's head, as shown in FIGS. 5A and 5B. The occipital support 52 accommodates a securely affixed occipital foam insert 72, which is configured to be positioned between the occipital support 52 and the base of the wearer's head. The occipital support 52 may also include a lower perpendicular member (not shown) to increase rigidity. The extreme distal ends of the lower edge of the occipital support 52 are integrally connected to opposing right and left lateral elongated vertical upper occipital adjustment supports 54. Preferably, the upper occipital adjustment supports 54 are injection molded and extend downwardly, substantially orthogonally, from the occipital support 52. Accordingly, the back upper plastic portion 51 is preferably formed from a single unitary piece of plastic.

The back lower plastic portion 61 includes a back support 62. The back support 62 is an essentially vertical surface that rests at or above the wearer's last or seventh cervical vertebra. In FIGS. 5A and 5B, the cervical spine region is designated as region Y and the thoracic spine region is designated as region Z. The back support 62 assists in the restriction of extension movement and accommodates a securely affixed back foam insert 74. The back support 62 may be curved to conform generally to the shape of the wearer's anatomy. For example, as shown in FIGS. 6A and 6B, the lower portion of the back support 62 may curve outwardly to conform to the wearer's upper back. The upper portion of the back support 62 may be curved to conform to the generally cylindrical shape of the wearer's neck. The upper portion of the back support 62 may have a width that is greater than the width of the lower portion of the back support 62. The distal ends of the upper edge of the back support 62 are integrally connected to opposing right and left lateral elongated vertical lower occipital adjustment supports 64. Preferably, the lower occipital adjustment supports 64 are injection molded, and extend upwardly from the back support 62. Accordingly, the back lower plastic portion 61 is preferably formed from a single unitary piece of plastic.

Similar to the upper and lower height adjustment supports 14, 24 of FIG. 2A, the terminal ends of the upper occipital adjustment supports 54 each include an outer surface, an inner surface, and opposing side surfaces with tabs extending inwardly toward each other, thereby forming a partially enclosed channel capable of slidably accepting the lower occipital adjustment support 64. The terminal end of each lower occipital adjustment support 64 is dimensionally similar to the inside dimension of the corresponding upper occipital adjustment support 54 to provide for a form-fitted, slidable connection between the lower occipital adjustment support 64 and the upper occipital adjustment support 54. Alternatively, the lower occipital adjustment supports 64 may be configured to slidably receive the upper occipital adjustment supports 54. The upper occipital adjustment supports 54 and lower occipital adjustment supports 64 collectively include a means for securely locking the upper occipital adjustment supports 54 with respect to the lower occipital adjustment supports 64. For example, each upper occipital adjustment support 54 may include an integrally connected, pivotably moveable lock tab 41 having a lock boss. Each lower occipital adjustment support 64 may include a series of lock openings 43 to accept the cooperative upper occipital adjustment support lock boss, and lock the back upper plastic portion 51 at a desired height with respect to the back lower plastic portion 61.

Similar to the sternum support 22 and front thoracic extender of FIG. 3, the back support 62 includes a slidably connected back thoracic extender 63. The terminal end of the back support 62 includes an outer surface, an inner surface, and opposing side surfaces with tabs extending inwardly toward each other, thereby forming a partially enclosed channel capable of accepting the back thoracic extender 63. The back thoracic extender 63 is a separate component, dimensionally similar to the inside dimension of the terminal end of the back support 62 to provide for a form-fitted, slidable connection between the back thoracic extender 63 and the back support 62. The back thoracic extender 63 includes a securely affixed back thoracic foam insert 76 to provide comfort to the wearer. The back support 62 and the back thoracic extender 63 collectively include a means for securely locking the back thoracic extender 63 with respect to the back support 62. For example, the back support 62 may include an integrally connected, pivotably moveable lock tab 41 having a lock boss. The lock tab 41 and the lock boss may also be securely affixed separate components. The back thoracic extender 63 may include a series of lock openings 43 to accept the cooperative back support lock boss, and lock the back thoracic extender 63 at a desired height with respect to the back support 62.

As shown in FIGS. 5A, 5B, 6A, and 6B, each lower occipital adjustment support 64 includes an area to securely affix a fastener material 78, such as hook-and-loop and the like. Preferably, each lower occipital adjustment support 64 includes a fastener material opening 79 to allow a free end of the fastener material 78 to be inserted, wrapped, and securely affixed to the lower occipital adjustment support 64. The fastener material 78 maintains a substantially horizontal alignment relative to the back portion 50. The other free end of the fastener material 78 extends beyond the distal end of the back portion 50, either along the outer or inner surface of the back foam insert 74, and engageably mates with the front portion fastener material 38. The back foam insert 74 includes portions that cover the right and left sides of the wearer's neck, and also includes a portion that extends to the central region of the wearer's upper back, below the back support 62.

When assembled, the back portion 60, as best shown in FIGS. 5A and 5B, includes a spinal access opening 70 which is defined by the lowermost edge of the occipital support 52, the proximal edges of the upper occipital adjustment supports 54, the proximal edges of the lower occipital adjustment supports 64 and the uppermost edge of the back support 62. The area of the spinal access opening 70 incrementally increases as the occipital support 52 is adjusted from a first lowest position, as shown in FIG. 5A, to a final highest position, as shown in FIG. 5B.

Figure 7A:
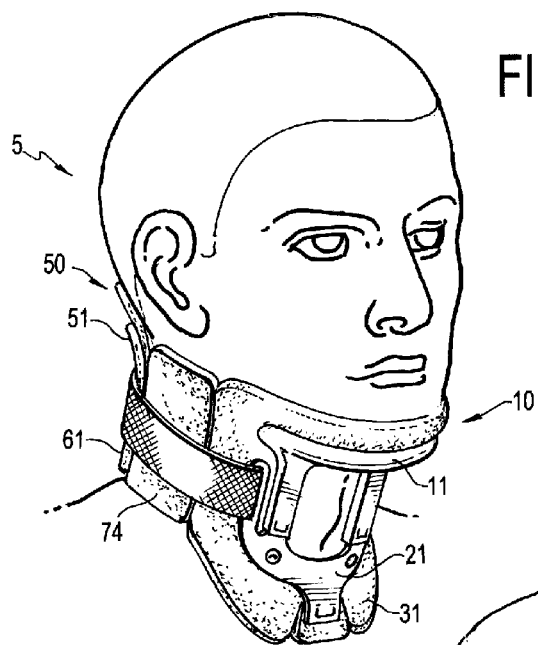
FIGS. 7A and 7B are perspective views of a cervical collar in accordance with an exemplary embodiment of the present invention.
Figure 7B:
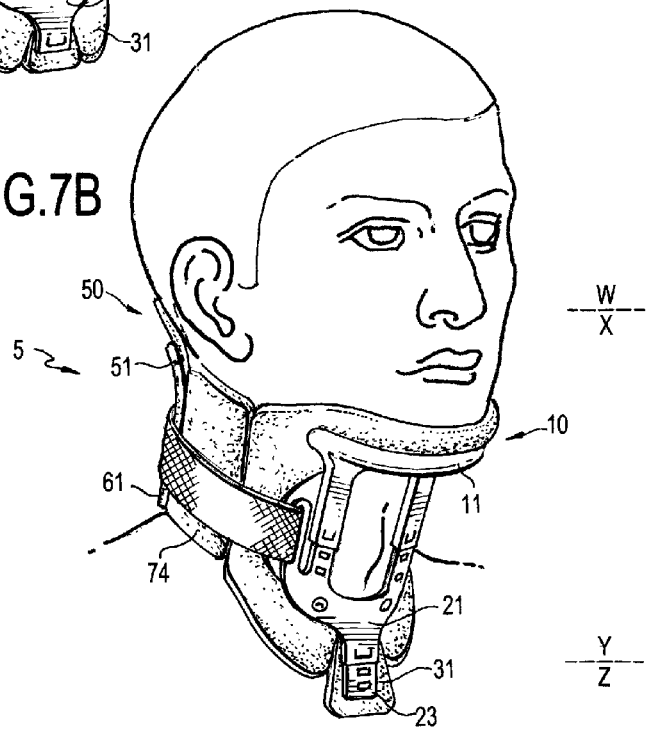

Turning to FIGS. 7A and 7B, the cervical collar 5, when assembled, includes front portion 10, with the front upper plastic portion 11 connected to the front lower plastic portion 21. The assembled cervical collar 5 further includes separate and distinct back portion 50, with the back upper plastic portion 51 connected to the back lower plastic portion 61. The individual components of the cervical collar 5 may be securely affixed to one another, either permanently or temporarily, by mechanical or chemical means such as adhesives, hook-and-loop, rivet bosses, rivets, stitching, welding or the like.

The cervical collar 5 has five independent adjustable features that allow the single cervical collar 5 to be manipulated to accommodate a wide variety of unique physical attributes of prospective wearers, and to achieve the required level of restrictiveness as determined by a responsible healthcare provider.

The first of the independent adjustable features is the front height adjustment. The height of a wearer's neck is measured from the base of the chin to the top of the sternum. The height of the front portion 10 may be adjusted by retracting and extending the upper height adjustment supports 14 and lower height adjustment supports 24. As shown in FIGS. 1A and 4A, when the upper and lower height adjustment supports 14, 24 are fully retracted, the height of the front portion 10 is at its minimum, and the front portion 10 is capable of accommodating a wearer with a short neck. As shown in FIGS. 1B and 4B, when the upper and lower height adjustment supports 14, 24 are fully extended, the height of the front portion 10 is at its maximum, and the front portion 10 is capable of accommodating a wearer with a tall neck. The front height adjustment locking means allows the height of the front portion 10 to be securely adjusted to various heights between the minimum and maximum heights of the front portion 10. Preferably, the cervical collar 5 is configured such that, when the height of the front portion 10 is adjusted, the front upper plastic portion 11, including the chin support 12, move upwardly or downwardly, while the front lower plastic portion 12, including the sternum support 22, remains fixed with respect to the wearer's upper chest.

The second of the independent adjustable features is the front thoracic extender feature. The front thoracic extender 23 may be adjusted by retracting and extending the front thoracic extender 23 in relation to the sternum support 22. As shown in FIGS. 1A and 4A, when the front thoracic extender 23 is fully retracted, the front portion 10 may sufficiently restrict flexion movement. However, when the front thoracic extender 23 is fully extended, as shown in FIGS. 1B and 4B, the front thoracic extender 23 preferably extends below top of the wearer's sternum, and into the thoracic region (into the region designated as region Z in FIGS. 1A and 1B) and essentially eliminates flexion movement. The front thoracic extender locking means allows the front thoracic extender 23 to be securely adjusted to various degrees of extension in relation to the sternum support 22.

The third of the independent adjustable features is the occipital adjustment. Occipital adjustment of the cervical collar 5 may be performed by retracting and extending the upper occipital adjustment supports 54 and lower occipital adjustment supports 64. As shown in FIGS. 5A and 6A, when the upper and lower occipital adjustment supports 54, 64 are fully retracted, the back portion 60 may sufficiently restrict extension movement. As shown in FIGS. 5B and 6B, when the upper and lower occipital adjustment supports 54, 64 are fully extended, the occipital support 52 extends from the wearer's occipital bone toward the wearer's parietal bone (from region X toward region W in FIGS. 5A and 5B), and the back portion 50 essentially eliminates extension movement. The occipital support adjustment locking means allows the occipital support 52 to be securely adjusted to various settings, thereby allowing for various degrees of restriction of extension movement. Preferably, the cervical collar 5 is configured such that, when the occipital support 52 moves upwardly or downwardly the back support 62 remains fixed with respect to the wearer's upper back.

The fourth of the independent adjustable features is the back thoracic extender feature. The back thoracic extender 63 may be adjusted by retracting and extending the back thoracic extender 63 in relation to the back support 62. As shown in FIGS. 5A and 6A, when the back thoracic extender 63 is fully retracted, the back portion 50 may sufficiently restrict extension movement. However, when the back thoracic extender 63 is fully extended, as shown in FIGS. 5B and 6B, the back thoracic extender 63 extends below the wearer's first thoracic vertebra (into the region designated as region Z in FIGS. 5A and 5B) and essentially eliminates extension movement. The back thoracic extender locking means allows the back thoracic extender 23 to be securely adjusted to various degrees of extension in relation to the back support 62.

The fifth of the independent adjustable features is the circumferential adjustment. The front portion 10 and back portion 50 are preferably connected to each other at their respective distal ends by adjustable mechanical fasteners, such as the front portion fastener material 38 and the back portion fastener material 78. The mating of the front portion fastener material 38 and the back portion fastener material 78 may be performed such that the desired circumference, based on the circumference of the base of the wearer's neck, of the cervical collar 5 is achieved.

When manipulated individually or in combination, each of the above adjustable features restricts the movement of the cervical spine by limiting flexion, extension, rotation, lateral bending, and any combinations thereof. Manipulation of the adjustable features may also be performed to provide the appropriate level of support of the head in a neutral or specifically designated position relative to the wearer's neck and back.

The construction of the cervical collar 5 allows for independent features to be adjusted, during use, without interfering with the operation of the cervical collar 5. For example, when the chin support 12 or the front thoracic extender 23 is adjusted, the remainder of the cervical collar 5 remains stationary with respect to the wearer. Similarly, when the occipital support 52 or the back thoracic extender 63 is adjusted, the remainder of the cervical collar 5 remains stationary with respect to the wearer. As shown in FIGS. 7A and 7B, this may be achieved, for example, by configuring the front foam insert 31 and the back foam insert 74 such that they securely wrap around the wearer's neck, but have curved edges so as not to extend laterally onto the wearer's shoulders. Furthermore, the front thoracic extender 23 may have a width that is significantly less than the width of the front lower plastic portion 21, so as to allow movement of front thoracic extender 23 that does not result in movement of the front lower plastic portion 21. The cervical collar 5 is configured such that during use, both the front lower plastic portion 21 and the back lower plastic portion 61 remain stationary with respect to the wearer. For example, adjustment of the front upper plastic portion 11 or the front thoracic extender 23 does not result in the movement of the front lower plastic portion 21. Similarly, adjustment of the back upper plastic portion 51 or the back thoracic extender 63 does not result in the movement of the back lower plastic portion 61.

In the exemplary embodiment of the cervical collar 5 shown in FIGS. 1A-7B, the incompressible plastic portions (i.e., the front upper plastic portion 11, the front lower plastic portion 21, the back upper plastic portion 51, and the back lower plastic portion 61) are relatively narrow at the front and back, respectively. Preferably, the front upper plastic portion 11 and the front lower plastic portion 21 are sufficiently wide to provide an adequate tracheal opening 30 and support for the chin support 12, and are narrower than the width of the wearer's mandible. In addition, the front upper height adjustment supports 14 are set inwardly relative to the extreme distal ends of the chin support 12. Thus, the plastic portions of the cervical collar 5 do not include any wing portions, thereby eliminating unnecessary material weight, so that incompressible plastic is not located at the sides of the wearer's neck. This allows for breathability of the cervical collar 5 in locations at which additional support may not be necessary. The relatively narrow widths of the front upper plastic portion 11, the front lower plastic portion 21, the back upper plastic portion 51, and the back lower plastic portion 52 allow those portions to be adjusted without interference by the wearer's shoulders. Because the cervical collar 5 is configured such that the front and back lower plastic portions 21, 61 remain stationary during use, the height of the cervical collar 5 may be adjusted (i.e., increased), without causing the cervical collar 5 to be lifted off of the shoulders of the wearer. To further increase the breathability of the cervical collar 5, and thereby the comfort of the wearer, the front foam insert 31 may be cut to include lateral openings 33. The fastener material 38 may be positioned over portions of the lateral openings 33. Therefore, patient compliance is achieved by the reasons of having a lightweight, breathable, multi-adjustable cervical collar which can be worn for extended periods of time without causing soreness or discomfort to the wearer.

As is shown in FIGS. 1A-7B, the front foam insert 31 may include an upper portion that is attached to the front upper plastic portion 11 at the chin support 12. The central part of the upper portion of the front foam insert 31 is positioned between the chin support 12 and the wearer's chin. The lateral parts of the upper portion of the front foam insert 31 extend rearward such that the distal ends of the upper portion of the front foam insert 31 are positioned approximately beneath the wearer's ear lobes. The upper portion of the front foam insert 31, therefore, essentially accommodates the entirety of the wearer's mandible. The front foam insert 31 may further include a lower portion that is attached to the front lower plastic portion 21 at the sternum support 22. The central part of the lower portion of the front foam insert 31 is positioned just above the wearer's sternum. The lateral parts of the lower portion of the front foam insert 31 extend rearward such that a lower edge of the front foam insert 31 passes approximately over the sternal ends of the wearer's clavicles, and the distal ends of the lower portion of the front foam insert 31 are positioned on the right and left sides of the base of the wearer's neck. The upper and lower portions of the front foam insert 31 are integrally connected at the distal ends of the front foam insert 31 (i.e., the front foam insert 31 is formed of a single piece of material). As shown, for example, in FIG. 4C, the distal ends of the front foam insert 31 may be positioned at the sides of the wearer's neck, between the wearer's neck and the lateral supports 16. The front foam insert 31 is configured such that the area of the lateral openings 33 increases as the height of the front portion 10 is increased.

Figure 8A:
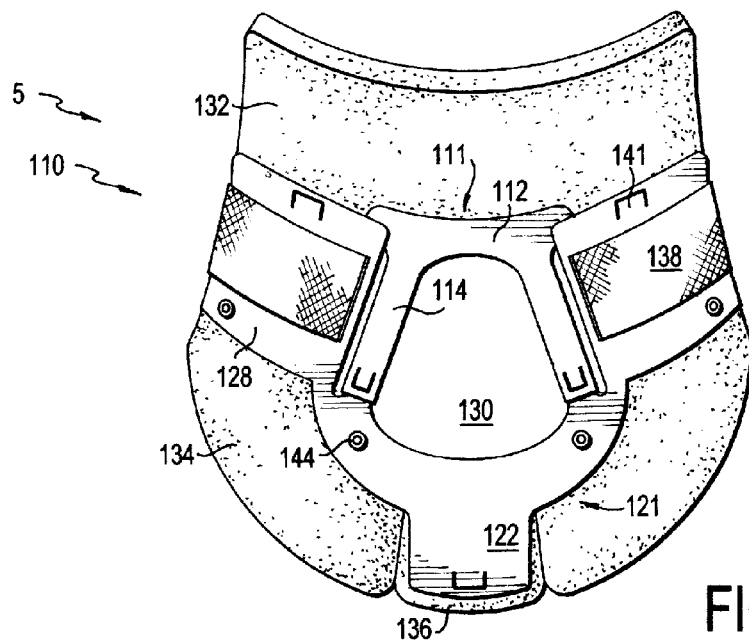
FIGS. 8A and 8B are front elevation views of the front portion of a cervical collar in accordance with an exemplary embodiment of the present invention.
Figure 8B:
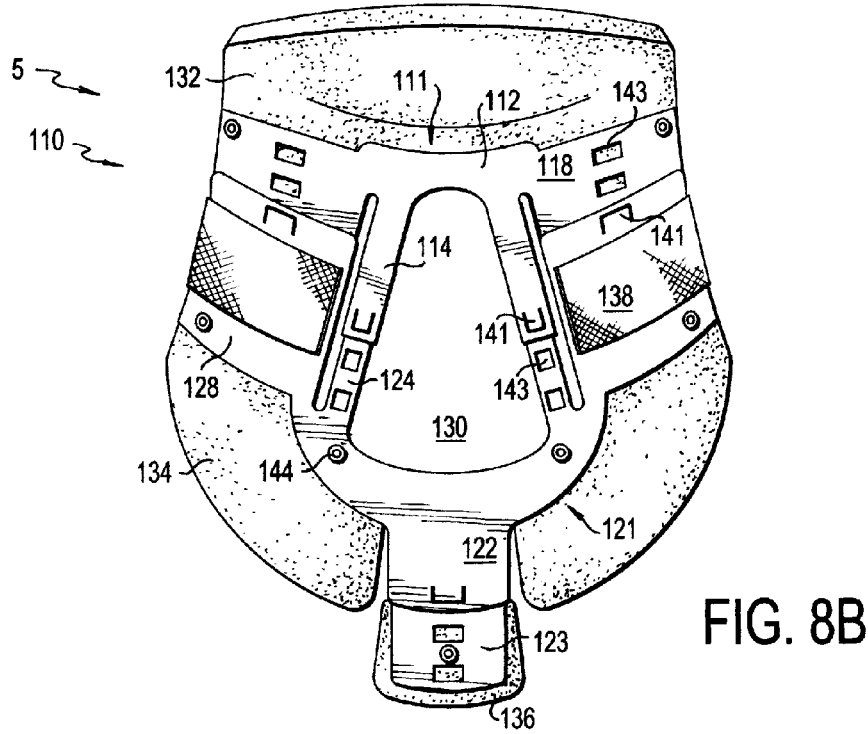

Turning to FIGS. 8A and 8B, shown therein is another embodiment of the front portion 110 of the cervical collar 5 of the present invention. In that embodiment, the front portion 110 includes a front upper plastic portion 111 and a front lower plastic portion 121. Preferably, the front upper plastic portion 111 and the front lower plastic portion 121 are fabricated from substantially incompressible plastic resin and injection molded in their final configurations as three dimensional components. The materials selected for the front upper plastic portion 111 and a front lower plastic portion 121 may be the same, or may be different. The front upper plastic portion 111 may accommodate a front upper foam insert 132. Fastening means 144, such as rivet bosses with cooperative rivets, may securely affix the front upper foam insert 132 to the front upper plastic portion 111.

Figure 9A:
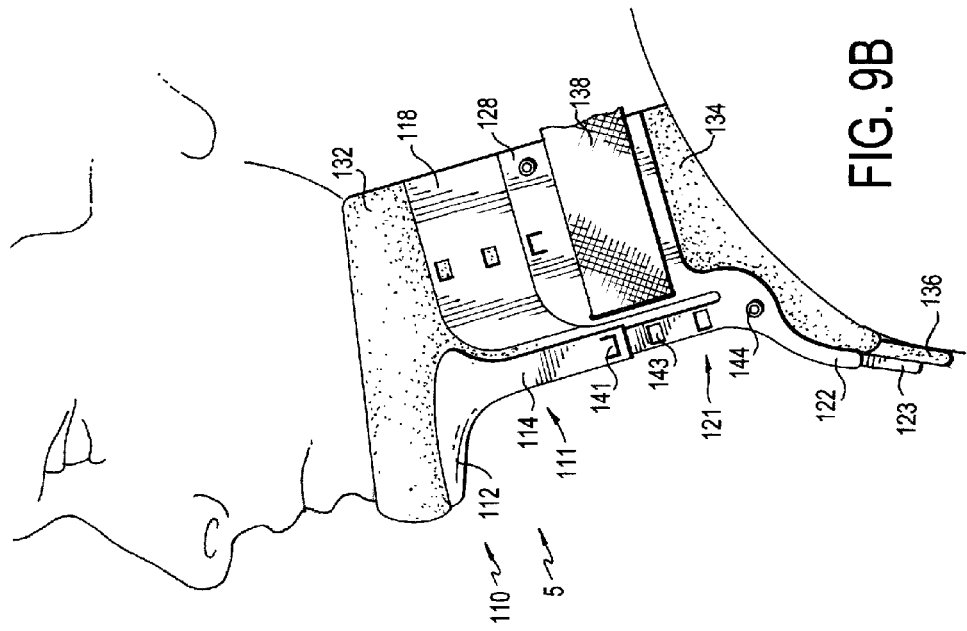
FIGS. 9A and 9B are side elevation views of the front portion of a cervical collar in accordance with an exemplary embodiment of the present invention.
Figure 9B:
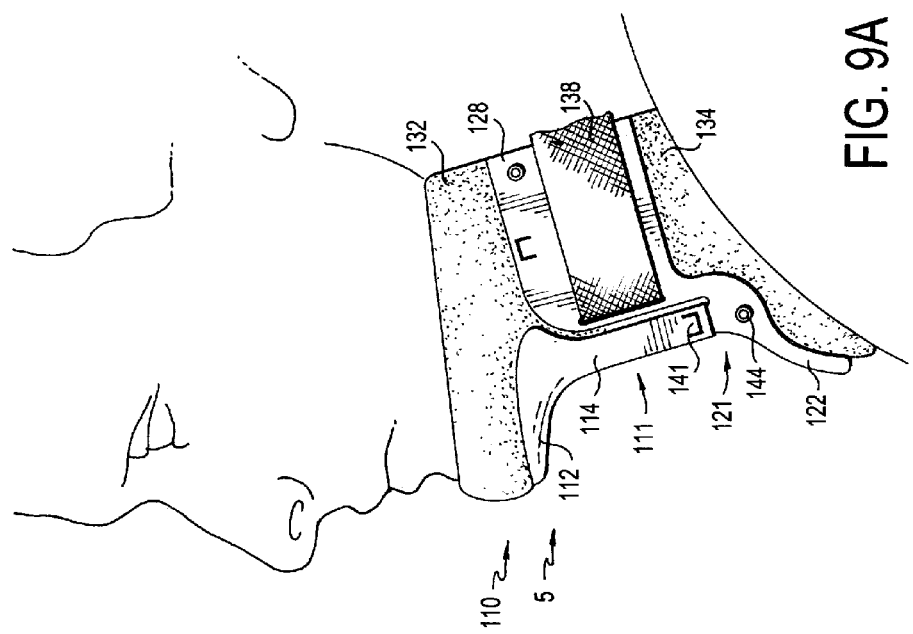
Figure 11A:
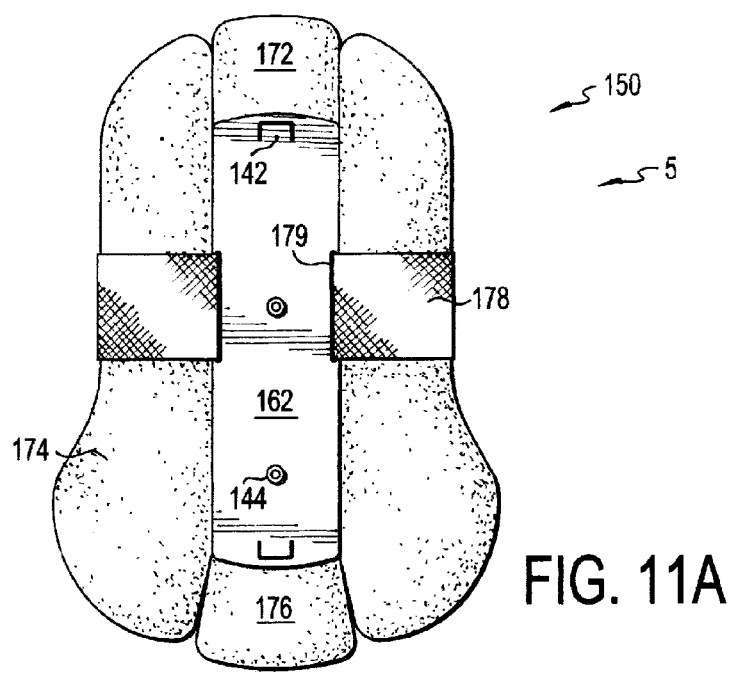
FIGS. 11A and 11B are rear elevation views of the back portion of a cervical collar in accordance with an exemplary embodiment of the present invention.
Figure 11B:
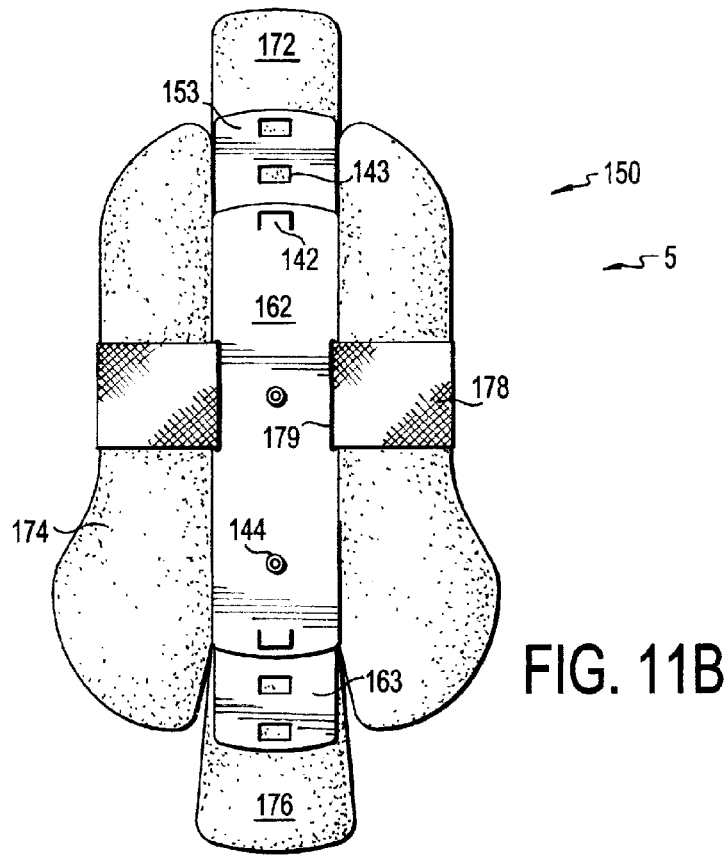
Figure 12B:
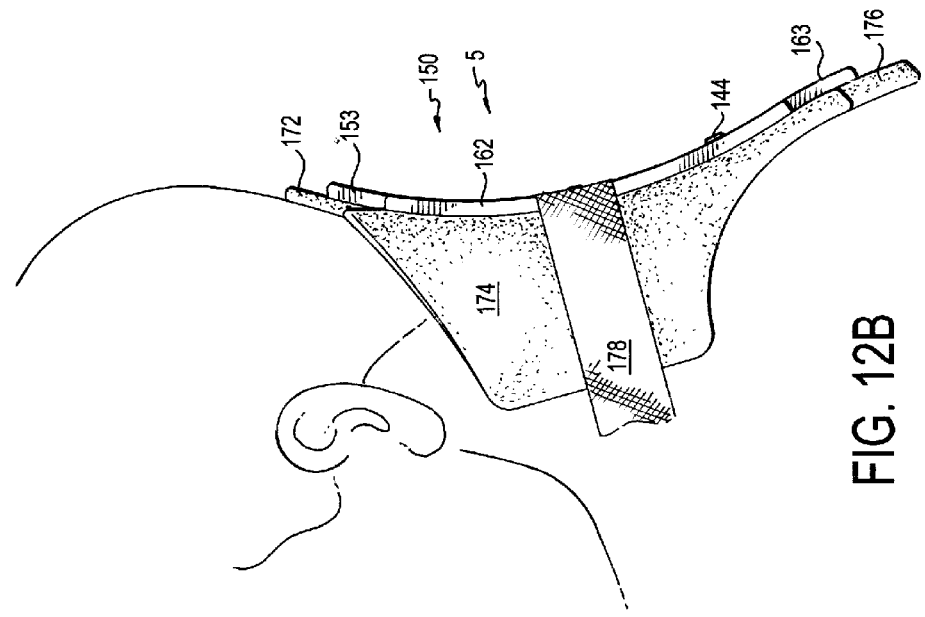
FIGS. 12A and 12B are side elevation views of the back portion of a cervical collar in accordance with an exemplary embodiment of the present invention.
Figure 12A:
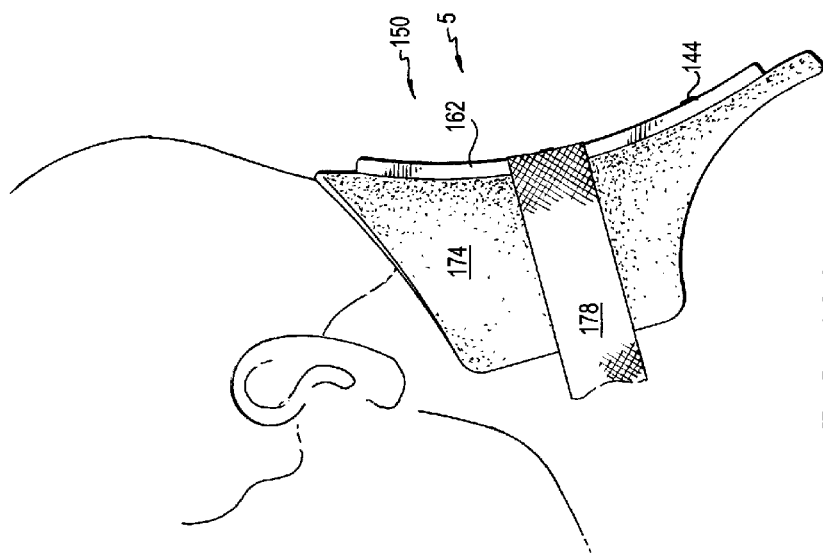
Figure 13A:
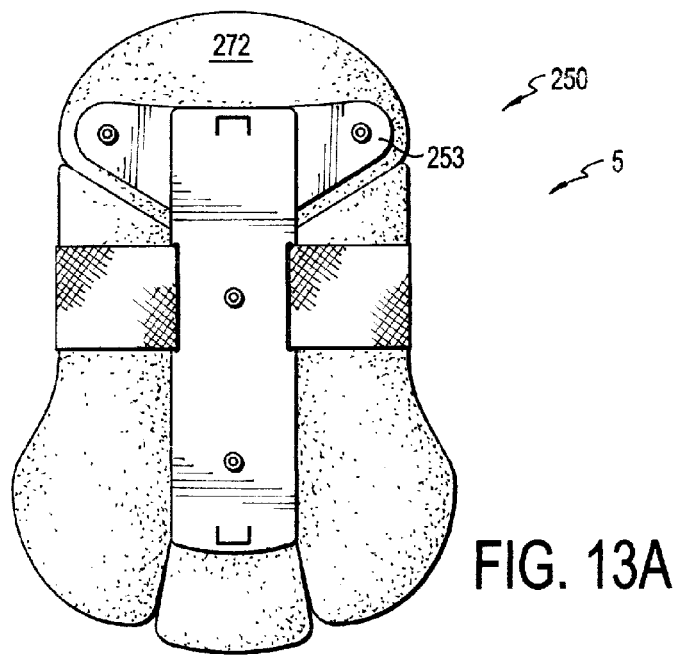
FIGS. 13A and 13B are rear elevation views of the back portion of a cervical collar in accordance with an exemplary embodiment of the present invention.
Figure 13B:
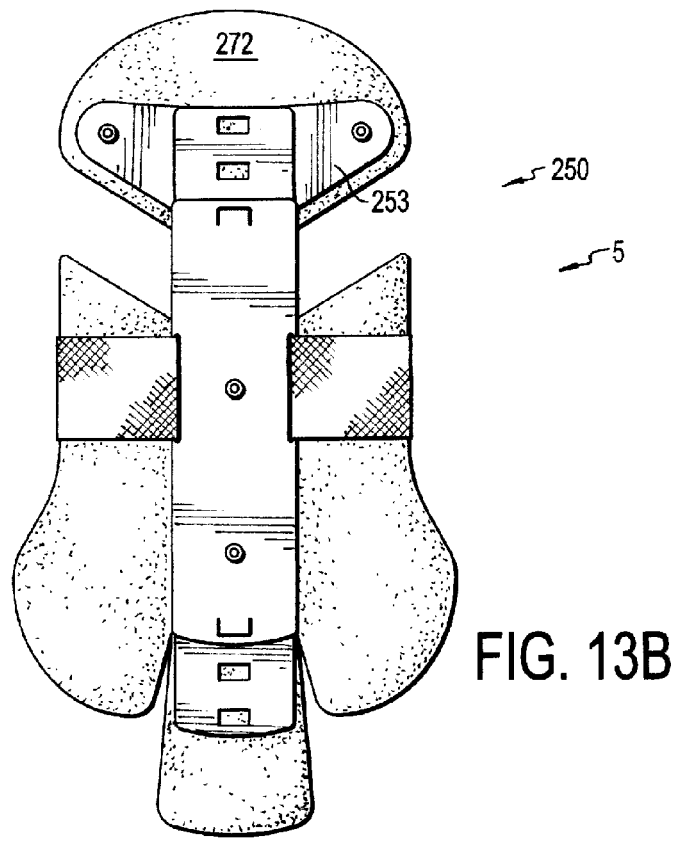
Figure 14B:
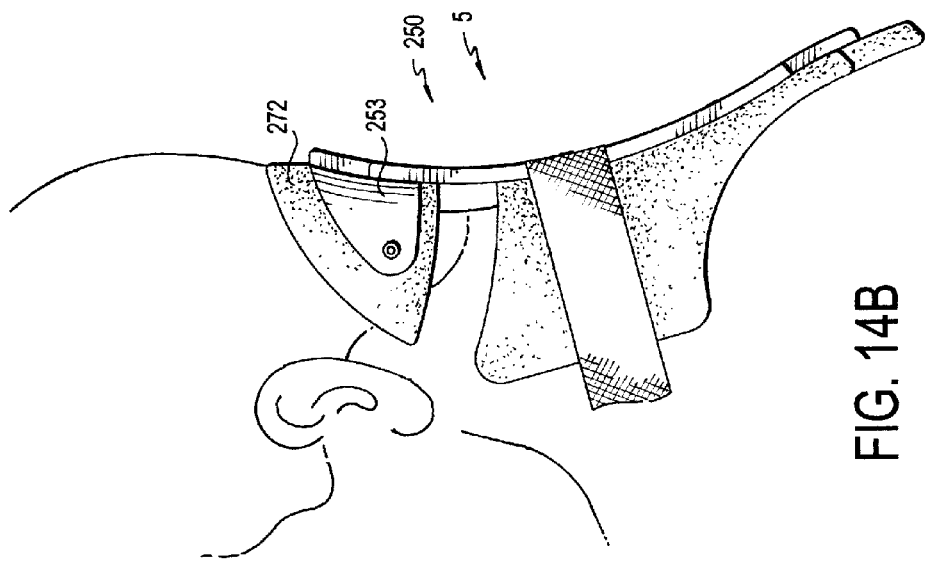
FIGS. 14A and 14B are side elevation views of the back portion of a cervical collar in accordance with an exemplary embodiment of the present invention.
Figure 14A:
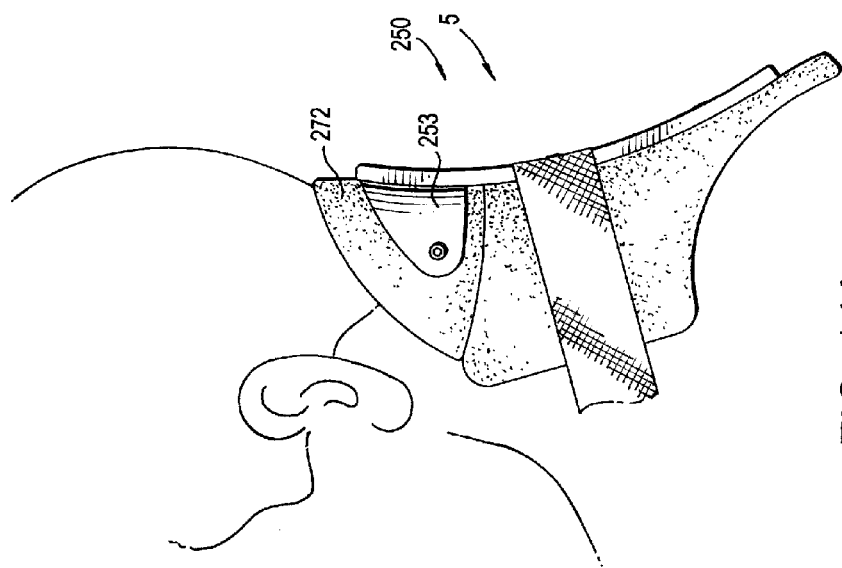

The front upper plastic portion 111 includes an upper central chin support 112 (similar to the chin support 12 described above), two opposing lateral upper height adjustment supports 114 (similar to the upper height adjustment supports 14 described above), and two opposing lateral upper wing portions 118. The distal ends of the chin support 112 may be integrally connected to the opposing right and left lateral upper wing portions 118, as shown in FIGS. 10A and 10B. Preferably, the upper wing portions 118 are injection molded, and may be curved to conform generally to the shape of the wearer's anatomy. Each upper wing portion 118 may include a demarcation or decreased thickness near the connection area between the upper wing portion 118 and the chin support 112. Alternatively, the upper wing portions 118 may be separate from the chin support 112, as shown in FIGS. 9A and 9B.

The front lower plastic portion 121 includes a central sternum support 122 (similar to the sternum support 22 described above), two opposing lateral lower height adjustment supports 124 (similar to the lower height adjustments 24 described above), a front thoracic extender 123 (similar to the front thoracic extender 23 described above) that accommodates a front thoracic foam insert 136, and two opposing lateral lower wing portions 128. The distal ends of the sternum support 122 are integrally connected to the opposing right and left lateral lower wing portions 128. Preferably, the lower wing portions 128 are injection molded, and may be curved to conform generally to the shape of the wearer's anatomy. Each lower wing portion 128 may include a demarcation or decreased thickness near the connection area between the lower wing portion 128 and the sternum support 122. The front lower plastic portion 121 may accommodate a front lower foam insert 134. Fastening means 144, such as rivet bosses with cooperative rivets, may securely affix the front lower foam insert 134 to the front lower plastic portion 121.

The upper wing portions 118 and lower wing portions 128 collectively include a means for securely locking the upper wing portions 118 with respect to the lower wing portions 128. For example, the medial section of each lower wing portion 128 may include a lock tab 141 having a lock boss. The medial section of each upper wing portion 118 may include a series of vertical lock openings to accept the lower wing portion lock boss. The distal ends of the upper wing portions 118 and the lower wing portions 128 may provide additional restriction of the wearer's lateral movement.

When assembled, the front portion 110, as best shown in FIGS. 8A and 8B, includes a tracheal opening 130 which is defined by the lowermost edge of the chin support 112, the proximal edges of the upper height adjustment supports 114, the proximal edges of the lower height adjustment supports 124, and the uppermost edge of the sternum support 122. The area of the tracheal opening 130 incrementally increases as the height of the front portion 110 is adjusted from a first lowest position, as shown in FIG. 8A, to a final highest position, as shown in FIG. 8B. In some instances, the front upper foam insert 132 and/or front lower foam insert 134 may partially extend into the tracheal opening 130 to provide additional comfort to the user.

FIGS. 9A and 10A show the front portion 110 configured such that the upper and lower height adjustment supports 114, 124, and the upper and lower wing portions 118, 128, are fully retracted. FIGS. 9B and 10B show the front portion 110 configured such that the upper and lower height adjustment supports 114, 124, and the upper and lower wing portions 118, 128, are fully extended.

Turning to FIGS. 11A, 11B, 12A, and 12B, shown therein is another exemplary embodiment of the back portion 150 of the cervical collar 5. Preferably, the back portion 150 includes components that are fabricated from substantially incompressible plastic resin and injection molded in their final configurations as three dimensional components. The plastic back portion 150 includes a back support 162 having an upper end, which includes a slidably connected occipital support 153, a central midsection, and a lower end, which includes a slidably connected back thoracic extender 163. The back support 162 may be curved to conform generally to the shape of the wearer's anatomy.

The occipital support 153 is configured to accept and support the base of a wearer's head and accommodate a securely affixed occipital foam insert 172 to provide comfort to the wearer. The upper end of the back support 162 includes an outer surface, an inner surface, and opposing side surfaces extending toward each other, thereby forming a partially enclosed channel capable of accepting the occipital support 153. The back thoracic extender 163 (similar to the back thoracic extender 63 above) is configured to accommodate a securely affixed back thoracic foam insert 176. The lower end of the back support 162 includes an outer surface, an inner surface, and opposing side surfaces extending toward each other, thereby forming a partially enclosed channel capable of accepting the back thoracic extender 163.

The back support 162, the occipital support 153, and the back thoracic extender 163 include means for securely locking the occipital support 153 and the back thoracic extender 163 with respect to the back support 162. For example, the back support may include lock tabs 141 having lock bosses. The occipital support 153 and the back thoracic extender 163 may include series of vertical lock openings 143 to accept the back portion lock bosses.

The distal edges of the centrally located midsection of the back support 162 contain fastener material openings 179, which permit the fastener material 178 to pass through and behind the back support 162, so that the fastener material 178 maintains a generally horizontal alignment relative to the back portion 150. The other free end of the fastener material 178 extends beyond the distal end of the back portion 150 either along the outer or inner surface of the back foam insert 174 and engageably mates to the front portion fastener material 138. Located on the midsection of the back support 162 is a fastening means 144, such as a rivet boss with a cooperative rivet, that securely affixes the fastener material 178 and the back foam insert 174 to the back support 162.

FIGS. 13A, 13B, 14A, and 14B illustrate another exemplary embodiment of the present invention in which the back portion 250 has an occipital support 253 and an occipital foam insert 272 configured to conform to the shape of a wearer's head, thereby providing additional support and comfort compared to the occipital support 153 and occipital foam insert 172 shown in FIGS. 11A, 11B, 12A, and 12B.

Figure 15B:
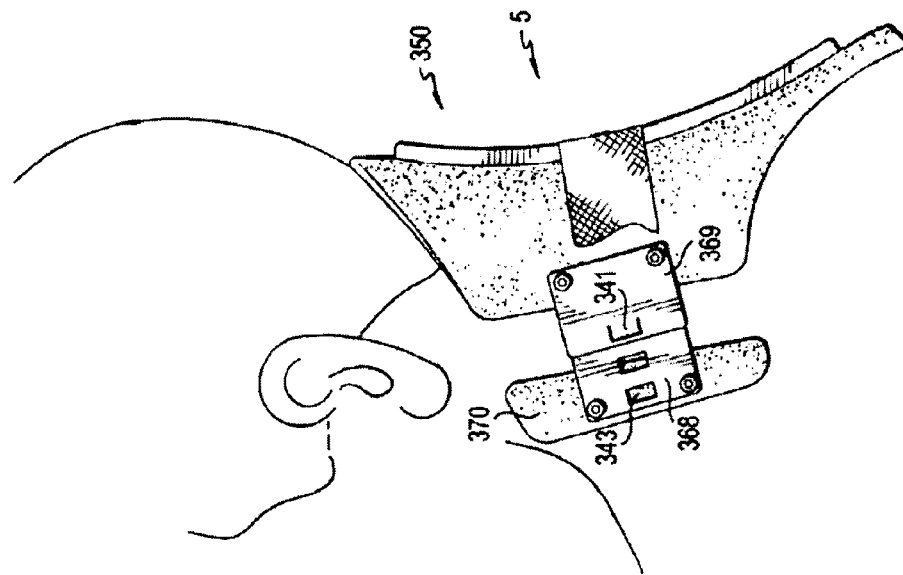
FIGS. 15A and 15B are side elevation views of the back portion, and part of the front portion, of a cervical collar in accordance with an exemplary embodiment of the present invention.
Figure 15A:
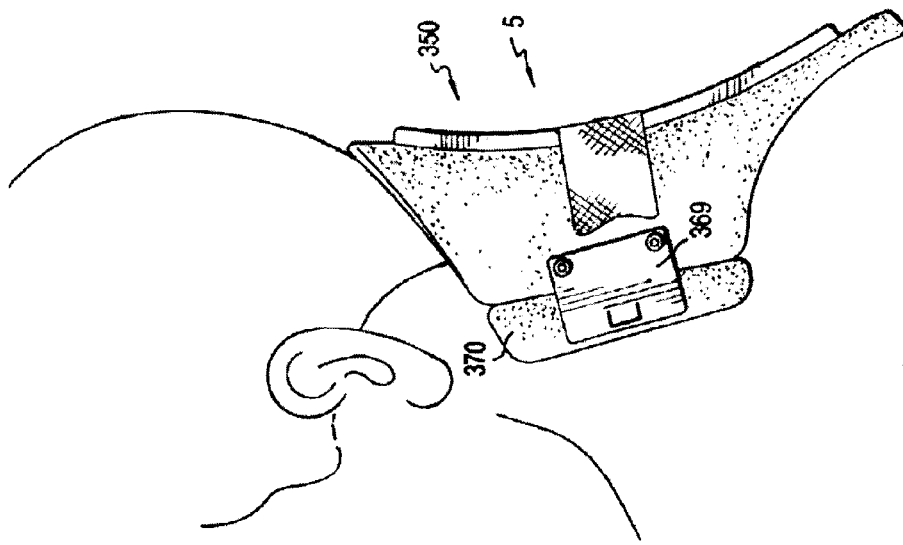
Figure 16A:
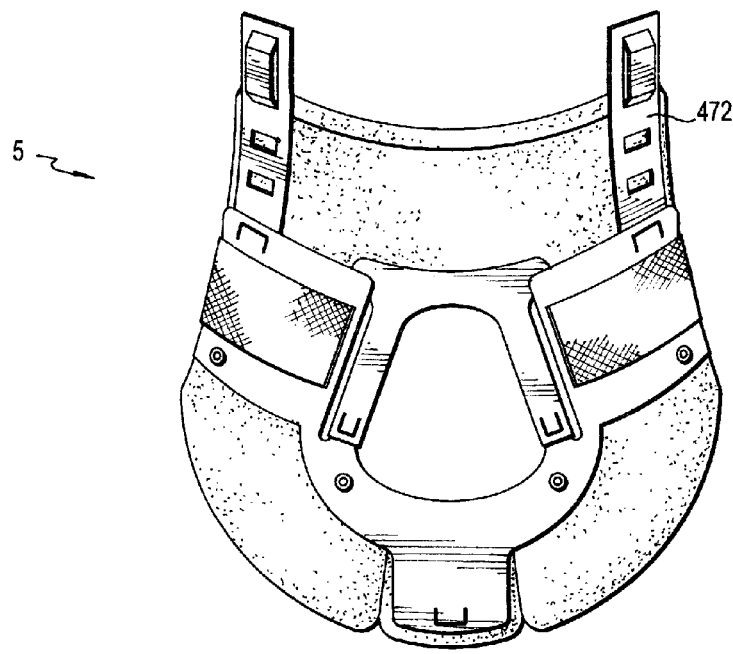
FIGS. 16A and 16B are front elevation views of the front portion of a cervical collar in accordance with an exemplary embodiment of the present invention.
Figure 16B:
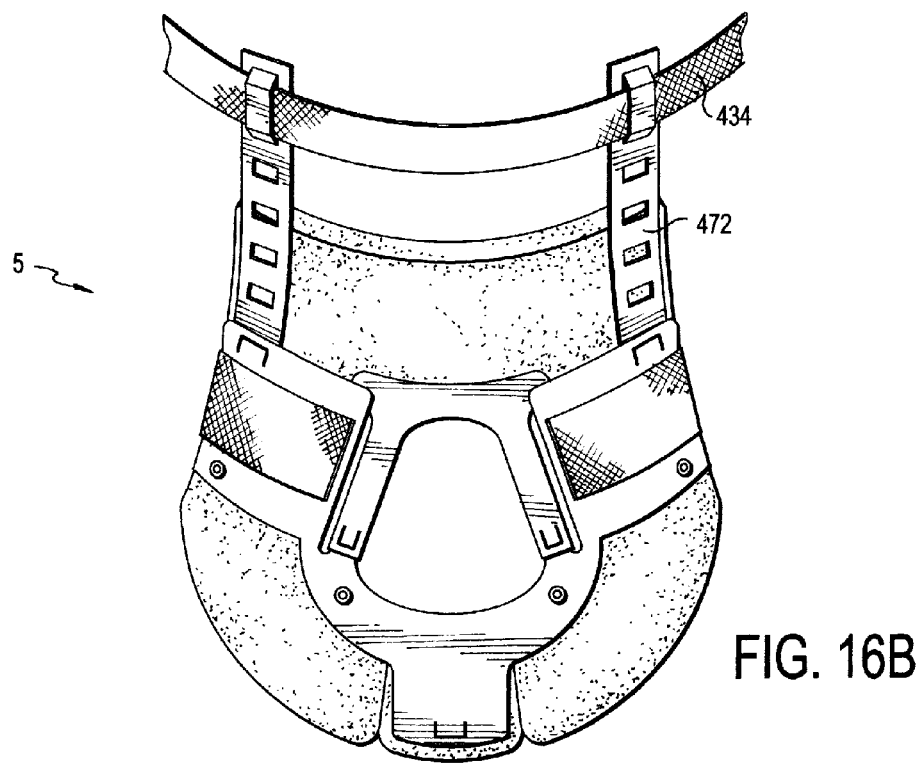
Figure 17:
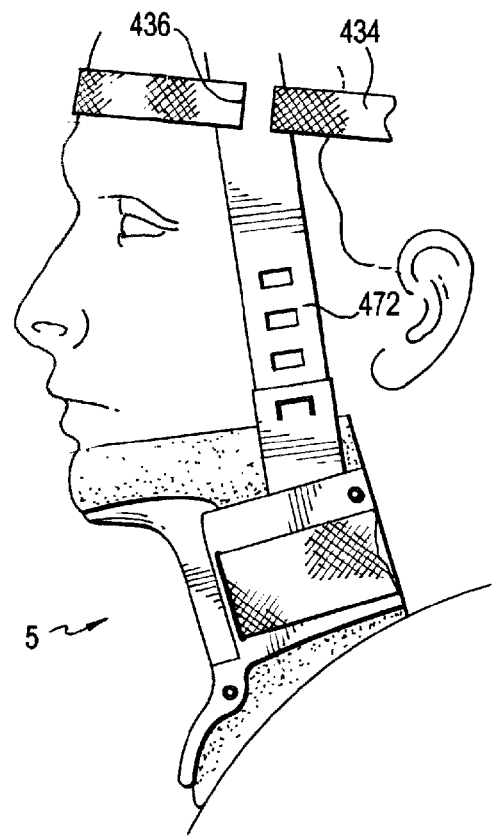
FIG. 17 is a side elevation view of the front portion of a cervical collar in accordance with an exemplary embodiment of the present invention.
Figure 18:
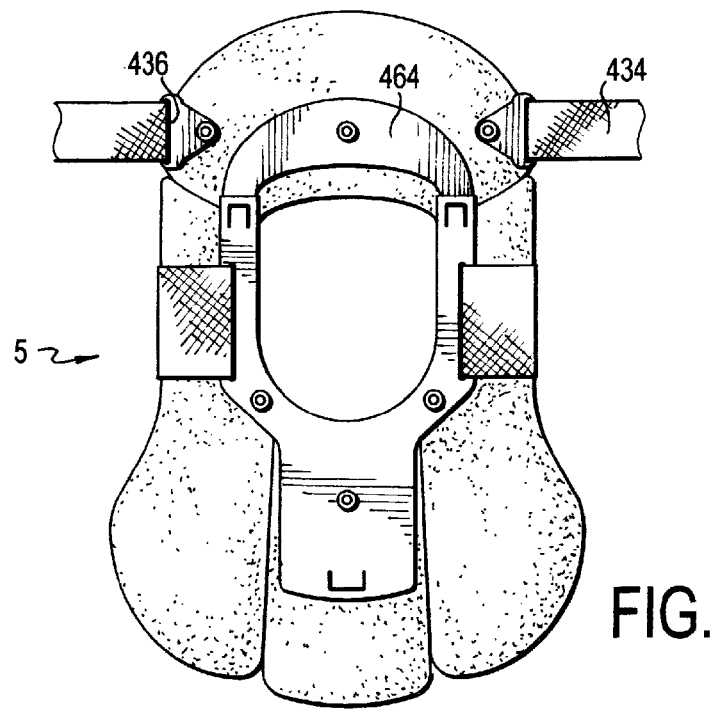
FIG. 18 is a rear elevation view of the back portion of a cervical collar in accordance with an exemplary embodiment of the present invention.

FIGS. 15A and 15B illustrate another exemplary embodiment of the present invention in which the back portion 350 and a back lateral support 370 are connected via a slidably engageable plastic back body portion 369 having a lock tab 341 with a lock boss, and a corresponding back lateral support portion 368 having lock openings 343 configured to accept the back body portion lock boss, thereby allowing the back lateral support 370 to be adjusted along the circumference of the wearer's neck to provide the proper amount of restriction to limit lateral movement.

FIGS. 16A, 16B, 17, and 18 illustrate another exemplary embodiment of the present invention in which the front portion 410 includes adjustable right and left frontal cranial restraint extenders 472, and the back portion 450 includes a back occipital support 464. A fastener material 434 further restricts rotation and lateral movement of the wearer when secured around the wearer's head. The cranial restraint extenders 472 and the occipital support 464 may include slotted openings 436 for receiving and securing the fastener material 434.

Figure 19:
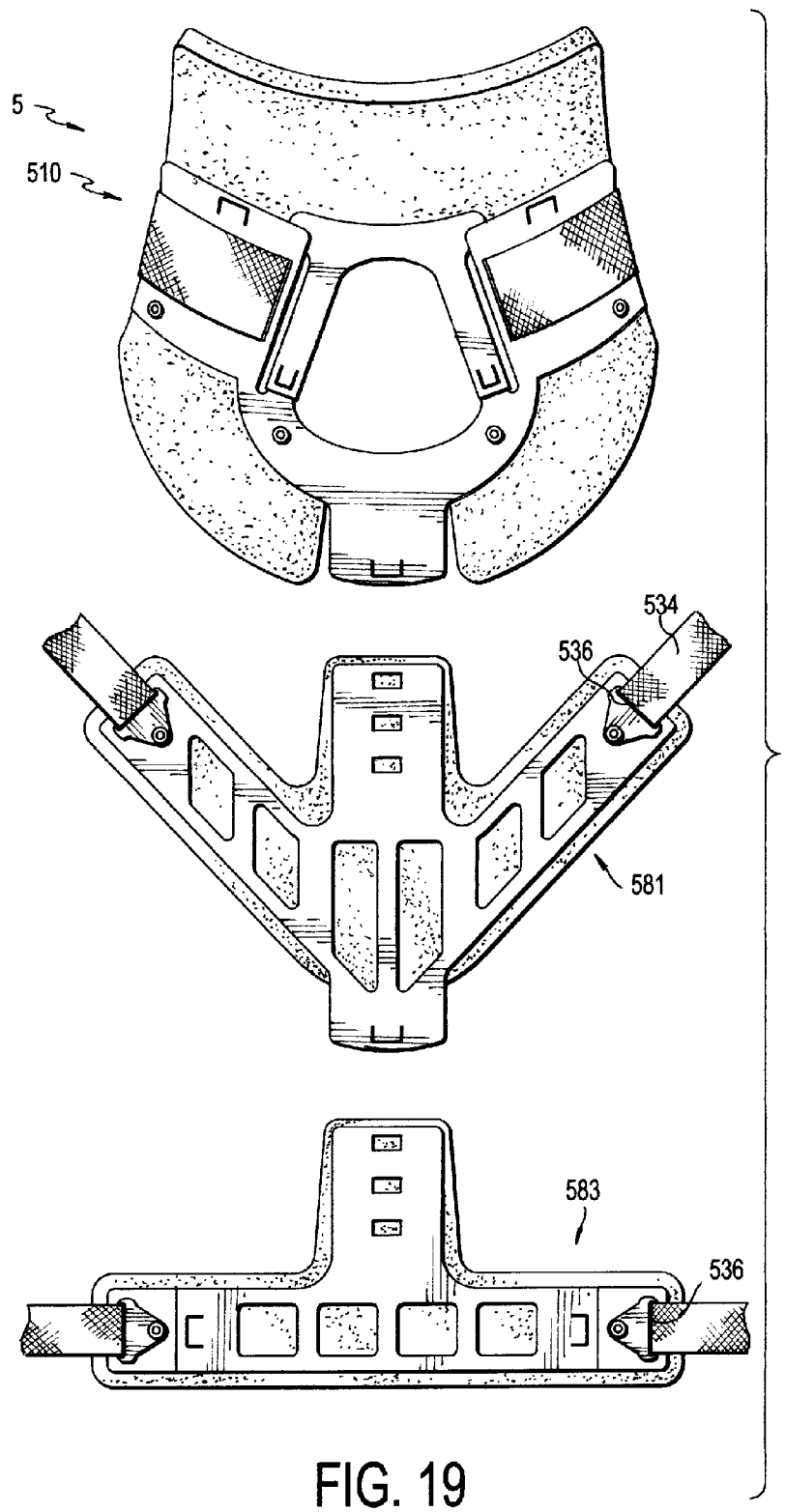
FIG. 19 is a side elevation view of the front portion of a cervical collar in accordance with an exemplary embodiment of the present invention.
Figure 20:
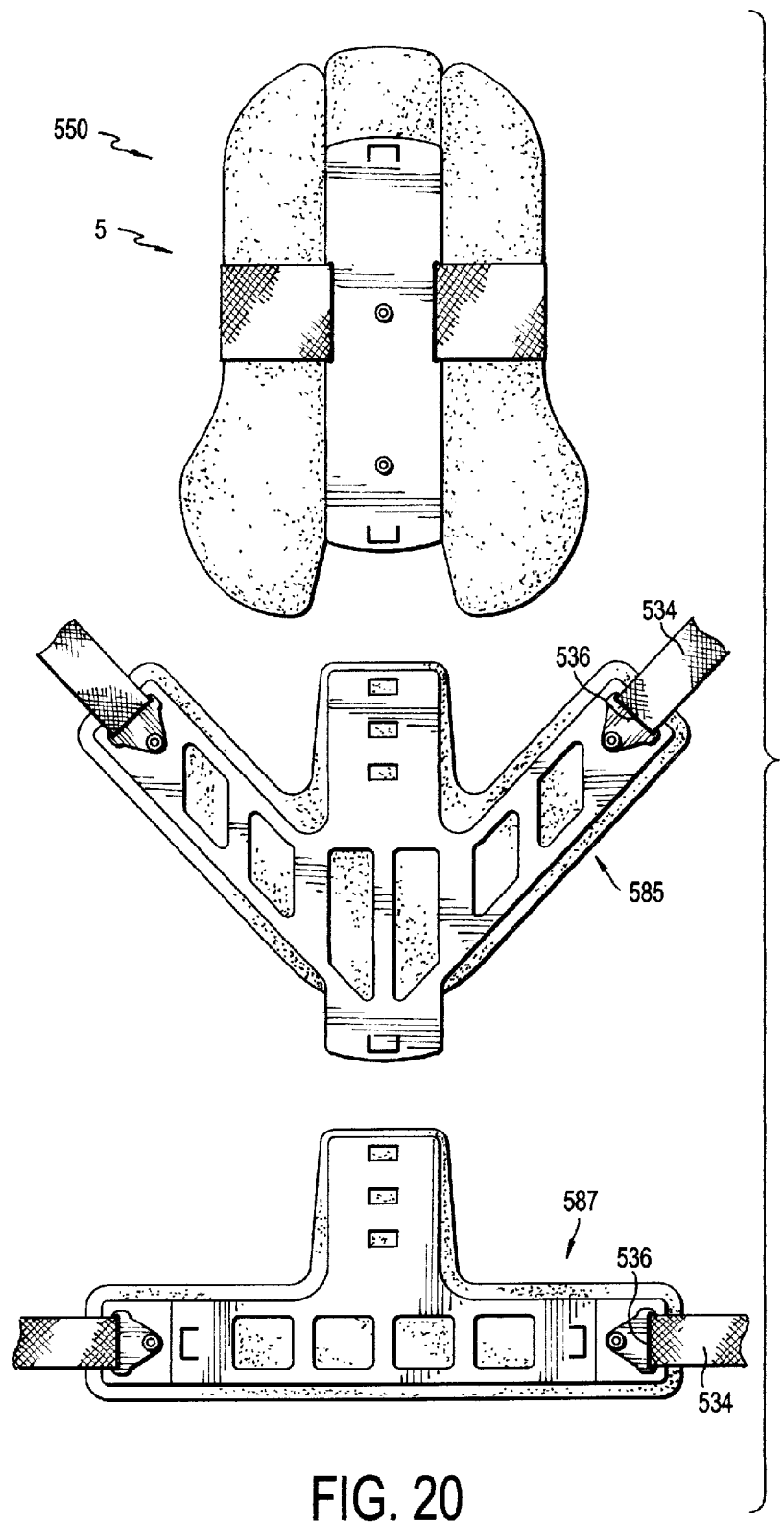
FIG. 20 is a side elevation view of the front portion of a cervical collar in accordance with an exemplary embodiment of the present invention.

FIGS. 19 and 20 illustrate another exemplary embodiment of the present invention in which the front portion 510 includes an adjustable front thoracic extender 581 and an adjustable front lumbar extender 583, each having moveable slotted openings 536 or swivel buckles for receiving a fastener material 534, which may be secured around the wearer's body. The front thoracic extender 581 and the front lumbar extender 583 are slidably engageable with one another, and include a means for securely locking the front thoracic extender 581 with respect to the front lumbar extender 583. The back portion 550 includes an adjustable back thoracic extender 585 and an adjustable back lumbar extender 587, each having moveable slotted openings 536 or swivel buckles for receiving a fastener material 534, which may be secured around the wearer's body. The back thoracic extender 585 and the back lumbar extender 587 are slidably engageable with one another, and include a means for securely locking the back thoracic extender 585 with respect to the back lumbar extender 587. When secured around the wearer's body, the front thoracic extender 581, the front lumbar extender 583, the back thoracic extender 585, and the back lumbar extender 587 further restrict flexion and extension of the wearer in the cervical thoracic and lumbar spinal regions. Each of those attachments may be used in combination or separately.

The cervical collar 5 has been described as having five adjustable features: (1) the front height adjustment provided by the front upper and lower height adjustment supports 14, 24; (2) the front thoracic extender 23; (3) the occipital support 52; (4) the back thoracic extender 63; and (5) the circumferential adjustment provided by the connection between the front and back portions 10, 50. In each of the embodiments of the cervical collar 5 described herein, the adjustable features are configured to operate independently of one another. Adjusting one feature does not affect the adjustment of the others. Together, all five of the independently adjustable features have a combined effect of proper fit and support of the cervical collar 5. Preferably, the cervical collar 5 includes at least two, and preferably all five of the adjustable features described herein. For instance, the cervical collar 5 may have a front height adjustment feature and a front thoracic adjustment feature, which adjusts separately from the front height adjustment feature. Those features are separately adjustable to accommodate the unique physical attributes of the heads and necks of various individual wearers. Furthermore, each individual adjustable feature of the cervical collar 5 can be separately retracted or extended to provide the commensurate amount of restriction required for a wearer to limit flexion, extension, rotation and lateral bending thus allowing the use of a single cervical collar 5 to be used throughout the wearer's recovery period. For example, after suffering an illness or injury, an individual would wear the cervical collar 5 with the adjustments set in their most restrictive positions. As the wearer recovers, the adjustable features of the cervical collar 5 may be independently manipulated to be less restrictive, thereby allowing for an increased range of motion as the wearer's level of activities increases.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A cervical collar comprising:
    a front portion including a first upper plastic portion, a first lower plastic portion, and a first thoracic extender;
    a sliding connection between the first upper plastic portion and the first lower plastic portion that allows the first upper plastic portion to be adjusted and secured with respect to the first lower plastic portion;
    a sliding connection between the first thoracic extender and the first lower plastic portion that allows the first thoracic extender to be adjusted and secured with respect to the first lower plastic portion;
    a back portion; and
    one or more fastener devices for connecting the front portion to the back portion,
    wherein the cervical collar is configured such that, when worn by a wearer, the front portion, the back portion, and the one or more fastener devices form an encircling band around the wearer's neck, and
    wherein the cervical collar is configured such that a height of the upper plastic portion with respect to the lower plastic portion is adjustable independent of adjustment of the first thoracic extender with respect to the first lower plastic portion.

2. The cervical collar of claim 1, wherein the back portion further comprises:
    a second upper plastic portion;
    a second lower plastic portion; and
    a sliding connection between the second upper plastic portion and the second lower plastic portion that allows the second upper plastic portion to be adjusted and secured with respect to the second lower plastic portion.

3. The cervical collar of claim 2, wherein the back portion further comprises:
    a second thoracic extender; and
    a sliding connection between the second thoracic extender and the second lower plastic portion that allows the second thoracic extender to be adjusted and secured with respect to the second lower plastic portion.

4. The cervical collar of claim 3, wherein the first and second thoracic extenders include a fastener material attached thereto, and wherein the fastener material is configured to be secured to a wearer's body.

5. The cervical collar of claim 4, further comprising:
    a first lumbar extender;
    a second lumbar extender;
    a sliding connection between the first lumbar extender and the first thoracic extender that allows the first lumbar extender to be adjusted and secured with respect to the first thoracic extender;
    a sliding connection between the second lumbar extender and the second thoracic extender that allows the second lumbar extender to be adjusted and secured with respect to the second thoracic extender;
    wherein the first and second lumbar extenders include a fastener material attached thereto, and wherein the fastener material is configured to be secured to a wearer's body.

6. The cervical collar of claim 2, further comprising padding fastened to the second upper plastic portion, and the second lower plastic portion, wherein the padding is formed of a different material than the first upper plastic portion, and the first lower plastic portion.

7. The cervical collar of claim 1, further comprising padding fastened to the first upper plastic portion, the first lower plastic portion, and the first thoracic extender, wherein the padding is formed of a different material than the first upper plastic portion, the first lower plastic portion, and the first thoracic extender.

8. The cervical collar of claim 1,
    wherein the one or more fastener devices allow the back portion to be adjusted and secured with respect to the front portion.

9. The cervical collar of claim 1, wherein the front portion further comprises a tracheal opening.

10. The cervical collar of claim 1, wherein the back portion further comprises a spinal access opening.

11. The cervical collar of claim 1, wherein each of the sliding connections includes a lock tab and a lock boss.

12. The cervical collar of claim 1, further comprising a separate right lateral support and a separate left lateral support.

13. The cervical collar of claim 1, further comprising:
    right and left upper wing portions disposed at opposite lateral ends of the first upper plastic portion;
    right and left lower wing portions disposed at opposite lateral ends of the first lower plastic portion;
    a sliding connection between the right upper wing portion and right lower wing portion that allows the right upper wing portion to be adjusted and secured with respect to the right lower wing portion; and
    a sliding connection between the left upper wing portion and the left lower wing portion that allows the left upper wing portion to be adjusted and secured with respect to the left lower wing portion.

14. The cervical collar of claim 1, wherein the cervical collar is configured such that adjustment of the first upper plastic portion and the first thoracic extender does not result in movement of the first lower plastic portion, when the cervical collar is worn by a wearer.

15. The cervical collar of claim 1, further comprising cranial restraint extenders having a fastener material attached thereto, wherein the fastener material is configured to be secured to a wearer's head.

16. The cervical collar of claim 1,
    wherein the cervical collar is configured such that, when worn by a wearer, the first lower plastic portion is configured to remain stationary with respect to the wearer during adjustment of the first upper plastic portion.

17. The cervical collar of claim 1,
    wherein the cervical collar is configured such that, when worn by a wearer, the first lower plastic portion is configured to remain stationary with respect to the wearer during adjustment of the first thoracic extender.

18. The cervical collar of claim 1, wherein the first upper plastic portion is formed from a single unitary piece of plastic, and wherein the first lower plastic portion is formed from a separate single unitary piece of plastic.

19. The cervical collar of claim 1, wherein the cervical collar comprises a chin support, and wherein the first upper plastic portion and the first lower plastic portion are narrower than the chin support.

20. A cervical collar comprising:
- a front portion having an upper height adjustment support, a lower height adjustment support adjustably connected to the upper height adjustment support, and a front thoracic extender adjustably connected to the lower height adjustment support;
- a back portion having an occipital support and a back thoracic extender; and
- one or more fastener devices for connecting the front portion to the back portion,
- wherein the upper height adjustment support and the lower height adjustment support are configured to allow a height of the cervical collar to be adjusted,
- wherein the one or more fastener devices are configured to allow a circumference of the cervical collar to be adjusted,
- wherein the height of the cervical collar, the circumference of the cervical collar, the front thoracic extender, the occipital support, and the back thoracic extender are each adjustable, independently of one another, and
- wherein the cervical collar is configured such that, when worn by a wearer, the front portion, the back portion, and the one or more fastener devices form an encircling band around the wearer's neck.

21. The cervical collar of claim 20, wherein the upper and lower height adjustment supports, the front thoracic extender, the occipital support, and the back thoracic extender are each slidably adjustable, and wherein the upper and lower height adjustment supports, the front thoracic extender, the occipital support, and the back thoracic extender each include a locking means.

22. The cervical collar of claim 20, wherein the front portion and the back portion each include a separate padding.

* * * * *